United States Patent
Bergmann

(10) Patent No.: US 11,530,276 B2
(45) Date of Patent: Dec. 20, 2022

(54) DPP3 BINDER DIRECTED TO AND BINDING TO SPECIFIC DPP3-EPITOPES AND ITS USE IN THE PREVENTION OR TREATMENT OF DISEASES / ACUTE CONDITIONS THAT ARE ASSOCIATED WITH OXIDATIVE STRESS

(71) Applicant: 4TEEN4 Pharmaceuticals GmbH, Hennigsdorf (DE)

(72) Inventor: Andreas Bergmann, Berlin (DE)

(73) Assignee: 4TEEN4 Pharmaceuticals GmbH, Hennigsdorf (DE)

( * ) Notice: Subject to any disclaimer, the term of this patent is extended or adjusted under 35 U.S.C. 154(b) by 112 days.

(21) Appl. No.: 16/758,881

(22) PCT Filed: Oct. 24, 2018

(86) PCT No.: PCT/EP2018/079197
§ 371 (c)(1),
(2) Date: Apr. 24, 2020

(87) PCT Pub. No.: WO2019/081595
PCT Pub. Date: May 2, 2019

(65) Prior Publication Data
US 2021/0206876 A1    Jul. 8, 2021

(30) Foreign Application Priority Data

Oct. 25, 2017 (EP) ................. 17198420

(51) Int. Cl.
*C07K 16/40* (2006.01)

(52) U.S. Cl.
CPC .......... *C07K 16/40* (2013.01); *C07K 2317/24* (2013.01); *C07K 2317/34* (2013.01); *C07K 2317/51* (2013.01); *C07K 2317/515* (2013.01); *C07K 2317/565* (2013.01); *C07K 2317/76* (2013.01); *C07K 2317/92* (2013.01); *C07K 2318/20* (2013.01)

(58) Field of Classification Search
CPC ............. C07K 16/40; C07K 2317/24; C07K 2317/34; C07K 2317/51; C07K 2317/515; C07K 2317/565; C07K 2317/76; C07K 2317/92; C07K 2318/20; A61K 2039/505
See application file for complete search history.

(56) References Cited

U.S. PATENT DOCUMENTS

2011/0319289 A1    12/2011 Libutti et al.

FOREIGN PATENT DOCUMENTS

| WO | 2005/106486 A2 | 11/2005 |
|----|----------------|---------|
| WO | 2007/117444 A2 | 10/2007 |
| WO | 2017/182561 A1 | 10/2017 |

OTHER PUBLICATIONS

Schroeder et al. (J Allergy Clin Immunol 2010, 125:S41-S52).*
Rudikoff et al. (Proc Natl Acad Sci USA 1982 Vol 79 p. 1979).*
Maccallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Piche-Nicholas et al. MABS 2018, 10:81-94.*
DaSilva et al. (Current Pharmaceutical Design, 2006, 12:4283-4293).*
International Search Report dated May 21, 2019 issued in corresponding PCT/EP2018/079197 application (8 pages).
S. Simaga et al., "Dipeptidyl Peptidase III in a Malignant and Non-Malignant Gynaecological Tissue", European Journal of Cancer, vol. 34, No. 3 (1998) pp. 399-405.
R.A. Kavishe et al., "Oxidative Stress in Malaria and Artemisinin Combination Therapy: Pros and Cons", The Febs Journal, vol. 284, No. 16 (2017) pp. 2579-2591.
I. Crandall et al., "The Human Anion Transport Protein, Band 3, Contains a CD36-Like Binding Domain for Plasmodium Falciparum-Infected Erythrocytes", Parasitology, vol. 112 (1996) pp. 261-267.
T. Chiba et al., "Inhibition of Recombinant Dipeptidyl Peptidase III by Synthetic Hemorphin-Like Peptides", Peptides, vol. 24, No. 5 (2003) pp. 773-778.

* cited by examiner

*Primary Examiner* — Sharon X Wen
(74) *Attorney, Agent, or Firm* — Millen, White, Zelano & Branigan, PC; Ryan Pool

(57) ABSTRACT

The present invention provides binder directed to and binding to a DPP3 protein or functional derivative thereof and its use in a method of prevention or treatment of diseases or acute conditions in a patient, wherein said disease or acute condition is associated with oxidative stress. With this context, specifically the present invention provides a binder being directed to and binding to an epitope according to SEQ ID NO.: 2, wherein said epitope is comprised in a DPP3 protein or a functional derivative thereof, and wherein said DPP3 binder recognizes and binds to at least three amino acids of SEQ ID NO.: 2.

Figure 1:
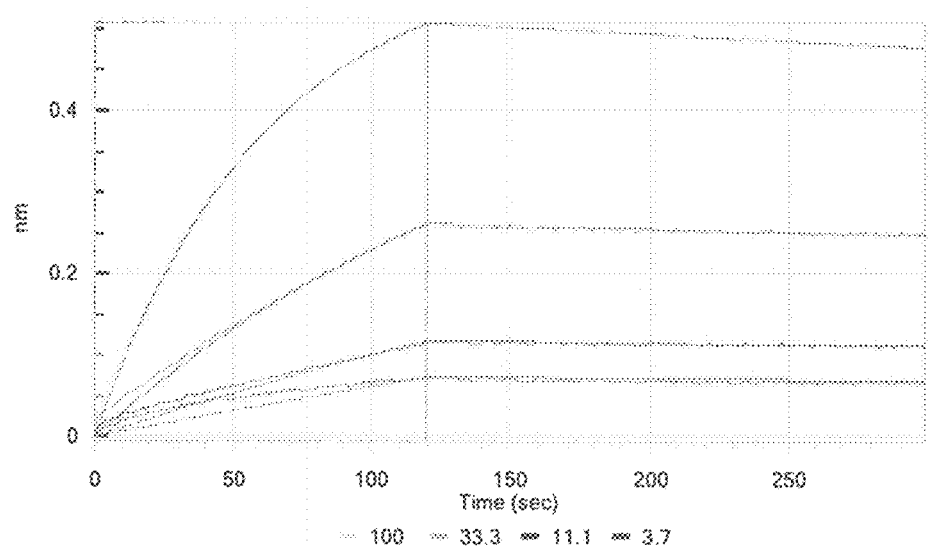
Figure 1:
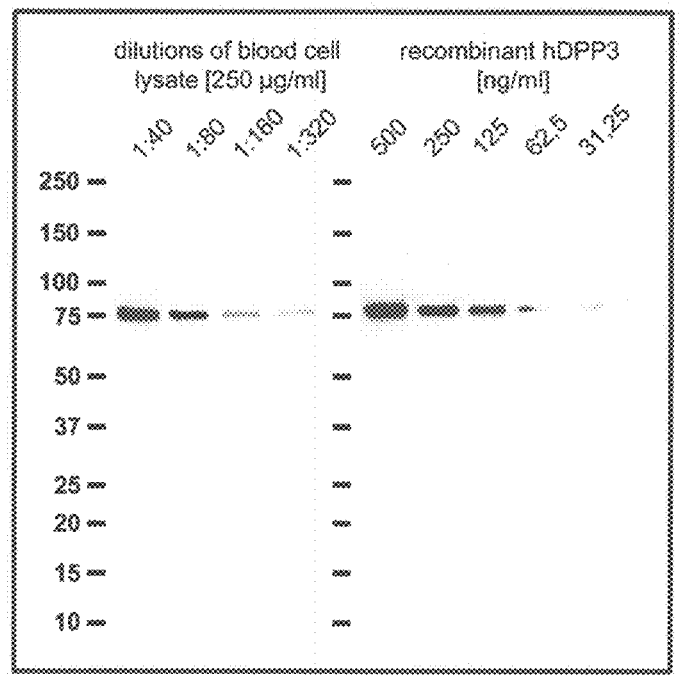
Figure 1:
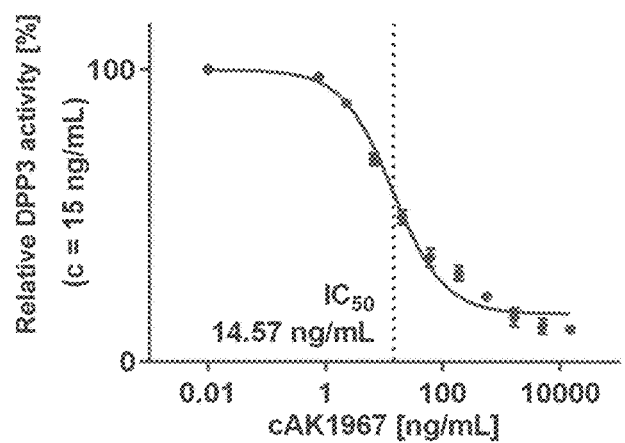

6 Claims, 4 Drawing Sheets
Specification includes a Sequence Listing.

mAbDPP3 = murine anti-DPP3 antibody

SEQUENCE LISTING

```
<160> NUMBER OF SEQ ID NOS: 13

<210> SEQ ID NO 1
<211> LENGTH: 737
<212> TYPE: PRT
<213> ORGANISM: Homo sapiens

<400> SEQUENCE: 1

Met Ala Asp Thr Gln Tyr Ile Leu Pro Asn Asp Ile Gly Val Ser Ser
1               5                   10                  15

Leu Asp Cys Arg Glu Ala Phe Arg Leu Leu Ser Pro Thr Glu Arg Leu
            20                  25                  30

Tyr Ala Tyr His Leu Ser Arg Ala Ala Trp Tyr Gly Gly Leu Ala Val
        35                  40                  45

Leu Leu Gln Thr Ser Pro Glu Ala Pro Tyr Ile Tyr Ala Leu Leu Ser
    50                  55                  60

Arg Leu Phe Arg Ala Gln Asp Pro Asp Gln Leu Arg Gln His Ala Leu
65                  70                  75                  80

Ala Glu Gly Leu Thr Glu Glu Glu Tyr Gln Ala Phe Leu Val Tyr Ala
                85                  90                  95

Ala Gly Val Tyr Ser Asn Met Gly Asn Tyr Lys Ser Phe Gly Asp Thr
            100                 105                 110

Lys Phe Val Pro Asn Leu Pro Lys Glu Lys Leu Glu Arg Val Ile Leu
        115                 120                 125

Gly Ser Glu Ala Ala Gln Gln His Pro Glu Glu Val Arg Gly Leu Trp
    130                 135                 140

Gln Thr Cys Gly Glu Leu Met Phe Ser Leu Glu Pro Arg Leu Arg His
145                 150                 155                 160

Leu Gly Leu Gly Lys Glu Gly Ile Thr Thr Tyr Phe Ser Gly Asn Cys
                165                 170                 175

Thr Met Glu Asp Ala Lys Leu Ala Gln Asp Phe Leu Asp Ser Gln Asn
            180                 185                 190

Leu Ser Ala Tyr Asn Thr Arg Leu Phe Lys Glu Val Asp Gly Glu Gly
        195                 200                 205

Lys Pro Tyr Tyr Glu Val Arg Leu Ala Ser Val Leu Gly Ser Glu Pro
    210                 215                 220

Ser Leu Asp Ser Glu Val Thr Ser Lys Leu Lys Ser Tyr Glu Phe Arg
225                 230                 235                 240

Gly Ser Pro Phe Gln Val Thr Arg Gly Asp Tyr Ala Pro Ile Leu Gln
                245                 250                 255

Lys Val Val Glu Gln Leu Glu Lys Ala Lys Tyr Ala Ala Asn Ser
            260                 265                 270

His Gln Gly Gln Met Leu Ala Gln Tyr Ile Glu Ser Phe Thr Gln Gly
        275                 280                 285

Ser Ile Glu Ala His Lys Arg Gly Ser Arg Phe Trp Ile Gln Asp Lys
    290                 295                 300

Gly Pro Ile Val Glu Ser Tyr Ile Gly Phe Ile Glu Ser Tyr Arg Asp
305                 310                 315                 320
```

```
Pro Phe Gly Ser Arg Gly Glu Phe Glu Gly Phe Val Ala Val Val Asn
                325                 330                 335
Lys Ala Met Ser Ala Lys Phe Glu Arg Leu Val Ala Ser Ala Glu Gln
                340                 345                 350
Leu Leu Lys Glu Leu Pro Trp Pro Pro Thr Phe Glu Lys Asp Lys Phe
                355                 360                 365
Leu Thr Pro Asp Phe Thr Ser Leu Asp Val Leu Thr Phe Ala Gly Ser
            370                 375                 380
Gly Ile Pro Ala Gly Ile Asn Ile Pro Asn Tyr Asp Asp Leu Arg Gln
385                 390                 395                 400
Thr Glu Gly Phe Lys Asn Val Ser Leu Gly Asn Val Leu Ala Val Ala
                405                 410                 415
Tyr Ala Thr Gln Arg Glu Lys Leu Thr Phe Leu Glu Glu Asp Asp Lys
                420                 425                 430
Asp Leu Tyr Ile Leu Trp Lys Gly Pro Ser Phe Asp Val Gln Val Gly
            435                 440                 445
Leu His Glu Leu Leu Gly His Gly Ser Gly Lys Leu Phe Val Gln Asp
            450                 455                 460
Glu Lys Gly Ala Phe Asn Phe Asp Gln Glu Thr Val Ile Asn Pro Glu
465                 470                 475                 480
Thr Gly Glu Gln Ile Gln Ser Trp Tyr Arg Ser Gly Glu Thr Trp Asp
                485                 490                 495
Ser Lys Phe Ser Thr Ile Ala Ser Ser Tyr Glu Glu Cys Arg Ala Glu
                500                 505                 510
Ser Val Gly Leu Tyr Leu Cys Leu His Pro Gln Val Leu Glu Ile Phe
            515                 520                 525
Gly Phe Glu Gly Ala Asp Ala Glu Asp Val Ile Tyr Val Asn Trp Leu
            530                 535                 540
Asn Met Val Arg Ala Gly Leu Leu Ala Leu Glu Phe Tyr Thr Pro Glu
545                 550                 555                 560
Ala Phe Asn Trp Arg Gln Ala His Met Gln Ala Arg Phe Val Ile Leu
                565                 570                 575
Arg Val Leu Leu Glu Ala Gly Glu Gly Leu Val Thr Ile Thr Pro Thr
                580                 585                 590
Thr Gly Ser Asp Gly Arg Pro Asp Ala Arg Val Arg Leu Asp Arg Ser
            595                 600                 605
Lys Ile Arg Ser Val Gly Lys Pro Ala Leu Glu Arg Phe Leu Arg Arg
610                 615                 620
Leu Gln Val Leu Lys Ser Thr Gly Asp Val Ala Gly Gly Arg Ala Leu
625                 630                 635                 640
Tyr Glu Gly Tyr Ala Thr Val Thr Asp Ala Pro Pro Glu Cys Phe Leu
                645                 650                 655
Thr Leu Arg Asp Thr Val Leu Leu Arg Lys Glu Ser Arg Lys Leu Ile
            660                 665                 670
Val Gln Pro Asn Thr Arg Leu Glu Gly Ser Asp Val Gln Leu Leu Glu
            675                 680                 685
Tyr Glu Ala Ser Ala Ala Gly Leu Ile Arg Ser Phe Ser Glu Arg Phe
            690                 695                 700
Pro Glu Asp Gly Pro Glu Leu Glu Glu Ile Leu Thr Gln Leu Ala Thr
705                 710                 715                 720
Ala Asp Ala Arg Phe Trp Lys Gly Pro Ser Glu Ala Pro Ser Gly Gln
                725                 730                 735
```

-continued

Ala

<210> SEQ ID NO 2
<211> LENGTH: 21
<212> TYPE: PRT
<213> ORGANISM: Homo sapiens

<400> SEQUENCE: 2

Cys Glu Thr Val Ile Asn Pro Glu Thr Gly Glu Gln Ile Gln Ser Trp
1               5                   10                  15

Tyr Arg Ser Gly Glu
            20

<210> SEQ ID NO 3
<211> LENGTH: 6
<212> TYPE: PRT
<213> ORGANISM: Homo sapiens

<400> SEQUENCE: 3

Ile Asn Pro Glu Thr Gly
1               5

<210> SEQ ID NO 4
<211> LENGTH: 4
<212> TYPE: PRT
<213> ORGANISM: Homo sapiens

<400> SEQUENCE: 4

Glu Thr Gly Glu
1

<210> SEQ ID NO 5
<211> LENGTH: 116
<212> TYPE: PRT
<213> ORGANISM: Mus musculus

<400> SEQUENCE: 5

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
        35                  40                  45

Trp Leu Ala His Ile Trp Trp Asn Asp Asn Lys Ser Tyr Asn Pro Ala
    50                  55                  60

Leu Lys Ser Arg Leu Thr Ile Ser Arg Asp Thr Ser Asn Asn Gln Val
65                  70                  75                  80

Phe Leu Lys Ile Ala Ser Val Val Thr Ala Asp Thr Gly Thr Tyr Phe
                85                  90                  95

Cys Ala Arg Asn Tyr Ser Tyr Asp Tyr Trp Gly Gln Gly Thr Thr Leu
            100                 105                 110

Thr Val Ser Ser
        115

<210> SEQ ID NO 6
<211> LENGTH: 112
<212> TYPE: PRT
<213> ORGANISM: Mus musculus

<400> SEQUENCE: 6

Asp Val Val Val Thr Gln Thr Pro Leu Ser Leu Ser Val Ser Leu Gly

```
                1               5                  10                  15
            Asp Pro Ala Ser Ile Ser Cys Arg Ser Ser Arg Ser Leu Val His Ser
                            20                  25                  30

Ile Gly Ser Thr Tyr Leu His Trp Tyr Leu Gln Lys Pro Gly Gln Ser
                        35                  40                  45

Pro Lys Leu Leu Ile Tyr Lys Val Ser Asn Arg Phe Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Leu Gly Val Tyr Phe Cys Ser Gln Ser
                                85                  90                  95

Thr His Val Pro Trp Thr Phe Gly Gly Gly Thr Lys Leu Glu Ile Lys
                            100                 105                 110
```

<210> SEQ ID NO 7
<211> LENGTH: 10
<212> TYPE: PRT
<213> ORGANISM: Mus musculus

<400> SEQUENCE: 7

```
Gly Phe Ser Leu Ser Thr Ser Gly Met Ser
1               5                   10
```

<210> SEQ ID NO 8
<211> LENGTH: 7
<212> TYPE: PRT
<213> ORGANISM: Mus musculus

<400> SEQUENCE: 8

```
Ile Trp Trp Asn Asp Asn Lys
1               5
```

<210> SEQ ID NO 9
<211> LENGTH: 8
<212> TYPE: PRT
<213> ORGANISM: Mus musculus

<400> SEQUENCE: 9

```
Ala Arg Asn Tyr Ser Tyr Asp Tyr
1               5
```

<210> SEQ ID NO 10
<211> LENGTH: 11
<212> TYPE: PRT
<213> ORGANISM: Mus musculus

<400> SEQUENCE: 10

```
Arg Ser Leu Val His Ser Ile Gly Ser Thr Tyr
1               5                   10
```

<210> SEQ ID NO 11
<211> LENGTH: 9
<212> TYPE: PRT
<213> ORGANISM: Mus musculus

<400> SEQUENCE: 11

```
Ser Gln Ser Thr His Val Pro Trp Thr
1               5
```

<210> SEQ ID NO 12
<211> LENGTH: 469
<212> TYPE: PRT

<213> ORGANISM: Mus musculus

<400> SEQUENCE: 12

Met Asp Pro Lys Gly Ser Leu Ser Trp Arg Ile Leu Leu Phe Leu Ser
1               5                   10                  15

Leu Ala Phe Glu Leu Ser Tyr Gly Gln Ile Thr Leu Lys Glu Ser Gly
            20                  25                  30

Pro Thr Leu Val Lys Pro Thr Gln Thr Leu Thr Leu Thr Cys Thr Phe
        35                  40                  45

Ser Gly Phe Ser Leu Ser Thr Ser Gly Met Ser Val Gly Trp Ile Arg
    50                  55                  60

Gln Pro Pro Gly Lys Ala Leu Glu Trp Leu Ala His Ile Trp Trp Asn
65                  70                  75                  80

Asp Asn Lys Ser Tyr Asn Pro Ala Leu Lys Ser Arg Leu Thr Ile Thr
                85                  90                  95

Arg Asp Thr Ser Lys Asn Gln Val Val Leu Thr Met Thr Asn Met Asp
            100                 105                 110

Pro Val Asp Thr Gly Thr Tyr Tyr Cys Ala Arg Asn Tyr Ser Tyr Asp
        115                 120                 125

Tyr Trp Gly Gln Gly Thr Leu Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

```
Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly
465

<210> SEQ ID NO 13
<211> LENGTH: 239
<212> TYPE: PRT
<213> ORGANISM: Mus musculus

<400> SEQUENCE: 13

Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Ser
            20                  25                  30

Val Thr Pro Gly Gln Pro Ala Ser Ile Ser Cys Lys Ser Ser Arg Ser
        35                  40                  45

Leu Val His Ser Ile Gly Ser Thr Tyr Leu Tyr Trp Tyr Leu Gln Lys
    50                  55                  60

Pro Gly Gln Ser Pro Gln Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

DPP3 BINDER DIRECTED TO AND BINDING TO SPECIFIC DPP3-EPITOPES AND ITS USE IN THE PREVENTION OR TREATMENT OF DISEASES / ACUTE CONDITIONS THAT ARE ASSOCIATED WITH OXIDATIVE STRESS

FIELD OF THE INVENTION

In a first major aspect of the invention, subject matter of the invention is a binder being directed to and binding to a dipeptidyl peptidase 3 (DPP3) protein or functional derivative thereof.

In another embodiment of the first major aspect of the invention, the aforementioned binder is provided for the use in the prevention or treatment of diseases or acute conditions in a patient, wherein said disease or acute condition is associated with oxidative stress.

In another embodiment of the first major aspect of the invention, the aforementioned binder is provided for use in the prevention or treatment of diseases or acute conditions in a patient, wherein said disease or acute condition is associated with oxidative stress, and wherein said diseases are selected from a group comprising neurodegenerative diseases, metabolic syndrome, cardiovascular disorders, autoimmune diseases, inflammatory lung diseases, kidney diseases, liver diseases, digestive diseases, viral infectious diseases, cancer, inflammation, sepsis, septic shock and SIRS.

In a second major aspect of the present invention, a binder is provided that is directed to and binding to an epitope according to SEQ ID NO.: 2, and wherein said binder recognizes and binds to at least three amino acids of SEQ ID NO.: 2, and wherein the epitope is comprised in DPP3 as depicted in SEQ ID NO.: 1.

The below text refers to the above second major aspect of the invention:

Additional subject matter of the invention is the aforementioned binder being directed to and binding to an epitope according to SEQ ID NO.: 2, wherein said binder is directed to and binding to an epitope according to SEQ ID NO.: 3, and wherein said binder recognizes and binds to at least three amino acids of SEQ ID NO.: 3, and wherein the epitope is comprised in DPP3 as depicted in SEQ ID NO.: 1.

Additional subject matter of the invention is the aforementioned binder being directed to and binding to an epitope according to SEQ ID NO.: 2, wherein said binder is directed to and binding to an epitope according to SEQ ID NO.: 4, and wherein said DPP3 binder recognizes and binds to at least three amino acids of SEQ ID NO.: 4, and wherein the epitope is comprised in DPP3 as depicted in SEQ ID NO.: 1.

Additional subject matter of the invention is the aforementioned binder being directed to and binding to an epitope according to SEQ ID NO.: 2, wherein said binder is selected from a group comprising an antibody or antibody fragment or non-Ig scaffold, and wherein the epitope is comprised in DPP3 as depicted in SEQ ID NO.: 1.

In a third major aspect of the invention, the above mentioned binder of the second major aspect of the invention that are directed to and binding to an epitope according to SEQ ID NO.: 2 is a dipeptidyl peptidase 3 (DPP3) binder directed to and binding to an epitope according to SEQ ID NO.: 2, wherein said epitope is comprised in a DPP3 protein or a functional derivative thereof, and wherein said DPP3 binder recognizes and binds to at least three amino acids of SEQ ID NO.: 2.

Additional subject matter of the invention is the aforementioned binder being directed to and binding to an epitope according to SEQ ID NO.: 2 according to the third aspect of the invention, wherein said binder is a monoclonal antibody or monoclonal antibody fragment, and wherein the complementarity determining regions (CDRs) in the heavy chain comprises the sequences:
SEQ ID NO.: 7, SEQ ID NO.: 8 and/or SEQ ID NO.: 9
and the complementarity determining regions in the light chain comprises the sequences:
SEQ ID NO.: 10, KVS and/or SEQ ID NO.: 11.

Additional subject matter of the invention is the aforementioned binder being directed to and binding to an epitope according to SEQ ID NO.: 2 according to the third aspect of the invention, wherein said binder is a humanized monoclonal antibody or humanized monoclonal antibody fragment, wherein the heavy chain comprises the sequence:
SEQ ID NO.: 12
and wherein the light chain comprises the sequence:
SEQ ID NO.: 13.

Additional subject matter of the invention is anyone of the aforementioned binder being directed to and binding to an epitope according to SEQ ID NO.: 2 for use in the prevention or treatment of diseases or acute conditions in a patient, wherein said disease or acute condition is associated with oxidative stress, and wherein the epitope is comprised in DPP3 as depicted in SEQ ID NO.: 1.

Specific subject matter of the present invention is a binder, specifically a dipeptidyl peptidase 3 (hereinafter DPP3) binder, directed to and binding to an epitope according to SEQ ID NO.: 2, wherein said epitope is comprised in a DPP3 protein or a functional derivative thereof, and wherein said DPP3 binder recognizes and binds to at least three amino acids (aa), preferably at least 4 aa of SEQ ID NO.: 2.

Further subject matter of the present invention is a binder, specifically a DPP3 binder, directed to and binding to an epitope according to SEQ ID NO.: 2, wherein said epitope is comprised in a DPP3 protein or a functional derivative thereof, and wherein said DPP3 binder recognizes and binds to at least three amino acids (aa), preferably at least 4 aa of SEQ ID NO.: 2, for use in the prevention or treatment of diseases or acute conditions of a patient, whereby said disease or acute condition is associated with oxidative stress.

Also, subject matter of the present invention is a binder, specifically an anti-DPP3 antibody or an anti-DPP3 antibody fragment, binding to an epitope according to SEQ ID NO.: 2, wherein said epitope is comprised in a DPP3 protein or a functional derivative thereof or an anti-DPP3 non-Ig scaffold binding to an epitope according to SEQ ID NO.: 2, wherein said epitope is comprised in a DPP3 protein or a functional derivative thereof, and wherein said anti-DPP3 antibody or anti-DPP3 antibody fragment or anti-DPP3 non-Ig scaffold recognizes and binds to at least three amino acids (aa), preferably at least 4 aa of SEQ ID NO.: 2.

With the above context, also subject matter of the present invention is a binder in accordance with the invention, specifically an anti-DPP3 antibody or an anti-DPP3 antibody fragment, binding to an epitope according to SEQ ID NO.: 2, wherein said epitope is comprised in a DPP3 protein or a functional derivative thereof or an anti-DPP3 non-Ig scaffold binding to an epitope according to SEQ ID NO.: 2, wherein said epitope is comprised in a DPP3 protein or a functional derivative thereof, and wherein said anti-DPP3 antibody or anti-DPP3 antibody fragment or anti-DPP3 non-Ig scaffold recognizes and binds to at least three amino acids (aa), preferably at least 4 aa of SEQ ID NO.: 2, for use in the prevention or treatment of diseases or acute conditions of a patient, whereby said disease or acute condition is associated with oxidative stress.

Further subject matter of the present invention is a method of prevention or treatment of diseases or acute conditions of a patient, whereby said disease or acute condition is associated with oxidative stress, characterized in that a binder directed to and binding to DPP3, or a binder being directed to and binding to SEQ ID.: 2 as epitope that is comprised in DPP3 protein or a functional derivative thereof, or an anti-DPP3 antibody or an anti-DPP3 antibody fragment binding to DPP3 or an anti-DPP3 non-Ig scaffold being directed to and binding to SEQ ID.: 2 as epitope that is comprised in DPP3 protein or a functional derivative thereof is administered to said patient in pharmaceutically effective amounts.

Subject matter of the present invention is further a pharmaceutical composition comprising a binder directed to and binding to DPP3, or a binder being directed to and binding to SEQ ID.: 2 as epitope that is comprised in DPP3 protein or a functional derivative thereof, or an anti-DPP3 antibody or an anti-DPP3 antibody fragment binding to DPP3 or an anti-DPP3 non-Ig scaffold being directed to and binding to SEQ ID.: 2 as epitope that is comprised in DPP3 protein or a functional derivative thereof for the use in the prevention or treatment of diseases or acute conditions of a patient, whereby said disease or acute condition is associated with oxidative stress.

Another subject of the present invention is a pharmaceutical composition comprising a binder of the invention, or a DPP3 binder in accordance with the invention, specifically an anti-DPP3 antibody or an anti-DPP3 antibody fragment binding to DPP3 or an anti-DPP3 non-Ig scaffold binding to DPP3 for use in the prevention or treatment of diseases or acute conditions of a patient, whereby said disease or acute condition is associated with oxidative stress as described above, and wherein said pharmaceutical composition comprises at least one additional pharmaceutically active drug which e.g. may be used as primary medicament in methods of treatment of a disease or acute condition and wherein said treatment induces oxidative stress as side effect, and thus the said binder, or DPP3 binder, anti-DPP3 antibody or the anti-DPP3 antibody fragment binding to DPP3 or the anti-DPP3 non-Ig scaffold binding to DPP3 may act as secondary medicament, which reduces or regulates the said induced oxidative stress.

A further embodiment of the invention is a kit comprising a binder, or a DPP3 binder in accordance with the invention, specifically an anti-DPP3 antibody or an anti-DPP3 antibody fragment binding to DPP3 or an anti-DPP3 non-Ig scaffold binding to DPP3 for use in the prevention or treatment of diseases or acute conditions of a patient, whereby said disease or acute condition is associated with oxidative stress as described above, and wherein said pharmaceutical composition optionally comprises at least one additional pharmaceutically active drug which e.g. may be used as primary medicament in methods of treatment of a disease or acute condition and wherein said treatment induces oxidative stress as side effect, and thus the said DPP3 binder, anti-DPP3 antibody or the anti-DPP3 antibody fragment binding to DPP3 or the anti-DPP3 non-Ig scaffold binding to DPP3 may act as secondary medicament, which reduces or regulates the said induced oxidative stress.

Modulating Anti-DPP3 Antibody, Fragment, Scaffold

Moreover, subject matter of the present invention is a binder in accordance with the invention, or an anti-DPP3 antibody or an anti-DPP3 antibody fragment binding to DPP3 or an anti-DPP3 non-Ig scaffold binding to DPP3 as described above for the use as a medicament, wherein said binder, or antibody or said antibody fragment or said non-Ig scaffold is a modulating binder, antibody or fragment or scaffold.

In a preferred embodiment said modulating anti-DPP3 antibody or a modulating anti-DPP3 fragment or a modulating non-Ig scaffold is used in the prevention or treatment of diseases or an acute condition in a patient, whereby said disease or acute condition is associated with oxidative stress.

Further, in accordance with the invention, said modulating anti-DPP3 antibody or an anti-DPP3 antibody fragment or a modulating non-Ig scaffold of the invention regulates the bioactivity of DPP3.

With the context of the invention, DPP3 bioactivity may be defined as the DPP3 enzyme activity or the regulating activity of DPP3 in the oxidative stress pathway.

In accordance with the invention, said modulating anti-DPP3 antibody or an anti-DPP3 antibody fragment or modulating non-Ig scaffold of the invention may enhance the bioactivity of DPP3.

In another embodiment of the invention, said modulating anti-DPP3 antibody or an anti-DPP3 antibody fragment or modulating non-Ig scaffold of the invention may reduce the bioactivity of DPP3.

In another specific embodiment with the context of the present invention, a "modulating" anti-DPP3 antibody or a modulating anti-DPP3 antibody fragment or a modulating non-Ig scaffold as described above is an anti-DPP3 antibody or an anti-DPP3 antibody fragment or a modulating anti-DPP3 non-Ig scaffold blocks the bioactivity of DPP3 at least 10%, preferably at least 50%, more preferably >50%, most preferably 100%.

In a specific embodiment a modulating binder, or modulating anti-DPP3 antibody or a modulating anti-DPP3 antibody fragment or a modulating anti-DPP3 non-Ig scaffold according to the present invention is used for the prevention or treatment of diseases or an acute condition of a patient, wherein said disease or acute condition is associated with oxidative stress.

Another embodiment of the present invention is a kit or an assay comprising the above described binder, or anti-DDP3 antibody, and/or an anti-DPP3 antibody fragment binding to DPP3 or an anti-DPP3 non-Ig scaffold binding to DPP3 for use in the prevention or treatment of a disease or acute condition of a patient, whereby said disease or acute condition is associated with oxidative stress.

BACKGROUND

Dipeptidyl peptidase 3 (DPP3)

Dipeptidyl peptidase 3—also known as Dipeptidyl aminopeptidase III, Dipeptidyl arylamidase III, Dipeptidyl peptidase III, Enkephalinase B or red cell angiotensinase; short name: DPP3, or DPPIII—is a metallopeptidase that removes dipeptides from physiologically active peptides, such as enkephalins and angiotensins. Hereinafter, the expression "DPP3" will be used throughout the text as abbreviated form of the above described dipeptidyl peptidase 3.

DPP3 was first identified and its activity measured in extracts of purified bovine anterior pituitary by Ellis & Nuenke, 1967. The enzyme, which is listed as EC 3.4.14.4, has a molecular mass of about 83 kDa and is highly conserved in procaryotes and eucaryotes (Prajapati & Chauhan, 2011).

The amino acid sequence of the human variant of DPP3 is depicted in SEQ ID No.: 1. DPP3 is a mainly cytosolic peptidase, which is ubiquitously expressed. Despite lacking a signal sequence, a few studies reported membranous activity (Lee & Snyder, 1982).

DPP3 is a zinc-depending exo-peptidase belonging to the peptidase family M49. It has broad substrate specificity for oligopeptides from three or four to ten amino acids of various compositions and is also capable of cleaving after proline. DPP3 is known to hydrolyze dipeptides from the N-terminus of its substrates, including angiotensin II, III and IV; angiotensin 1-7 (Cruz-Diaz et al., 2016); Leu- and Met-enkephalin; endomorphin 1 and 2. The metallopeptidase DPP3 has its activity optimum at pH 8.0-9.0 and can be activated by addition of divalent metal ions, such as $Co^{2+}$ and $Mg^{2+}$. Structural analysis of DPP3 revealed the catalytic motifs HELLGH (hDPP3 450-455) and EECRAE (hDPP3 507-512), as well as the following amino acids, that are important for substrate binding and hydrolysis: Glu 316, Tyr 318, Asp 366, Asn 391, Asn 394, His 568, Arg 572, Arg 577, Lys 666 and Arg 669 (Prajapati & Chauhan, 2011; Kumar et al., 2016; numbering refers to the sequence of human DPP3, see SEQ ID No.: 1). Considering all known amino acids or sequence regions that are involved in substrate binding and hydrolysis, the active site of human DPP3 can be defined as the region between amino acids 316 and 669.

Recent findings for DPP3 indicate its role for being a part of the protein metabolism but also playing a role in blood pressure regulation, pain modulation, inflammatory processes and oxidative stress regulation (Prajapati & Chauhan, 2011).

DPP3 has been also shown to be a promising biomarker in several publications. It has been shown that DPP3 activity is elevated in homogenates of ovarian and endometrial tumors. DPP3 activity even increases with the severity/malignancy of said tumors (Simaga et al., 1998 and 2003) Immune histology and western blot analysis of glioblastoma cell lines also revealed elevated DPP3 levels (Singh et al., 2014).

DPP3 was also proposed to be a potential arterio-risk marker (US 2011008805) and as a marker for rheumatoid arthritis (US 2006177886). The patent application WO 2005/106486 describes DPP3-expression and activity as diagnostic marker and DPP3 as therapeutic target in all kinds of diseases, due to ubiquitous expression of DPP3 in or at surface of cell. EP 1498480 mentions the potential diagnostic and therapeutic use of hydrolytic enzymes, including DPP3.

The relevant prior art can be further summarized as follows:

WO 2005/106486 describes in a general manner a method of screening for therapeutic agents which may be useful in the treatment of diseases, comprising cardiovascular diseases, infections, respiratory diseases, cancer, endocrinological diseases, metabolic diseases, gastroenterological diseases, inflammation, haematological diseases, muscle skeleton diseases, neurological and urological diseases. In said method of screening, a test compound is contacted with a DPP3 polynucleotide and the binding between said test compound and said DPP3 polynucleotide is detected. Further, the document describes in a general manner compounds, which may bind to and/or activate or inhibit the activity of DPP3. Further, the invention describes pharmaceutical compositions, which comprise such compounds.

Liu et al. 2007 describe a relation between activation of the antioxidant response element (ARE) and overexpression of DPP3 and Sequestome 1 in IMR-32 cells. Overexpression of DPP3 and Sequestome 1 stimulated the Nrf2 translocation and led to increased levels of NAD(P)H:quinone oxireductase 1, a protein which is transcriptionally regulated by the ARE.

Hast et al. 2013 describe a comparison of the spectrum of KEAP1 interacting proteins with the genomic profile of 178 squamous cell lung carcinomas characterized by The Cancer Genome Atlas and reveal amplification and mRNA overexpression of the DPP3 gene in tumors with high Nrf2activity but lacking Nrf2 stabilizing mutations. They further describe that tumor-derived mutations in KEAP1 are hypomorphic with respect to Nrf2 inhibition and that DPP3 over-expression in the presence of these mutants further promotes Nrf2 activation.

Overexpression of DPP3

Thus, according to the prior art, overexpression of intracellular DPP3 is known to be closely linked to oxidative stress regulation. DPP3 was identified as an activator of the antioxidant response element (ARE) in an unbiased screen of a cDNA library consisting of approximately 15,000 full-length human expression cDNAs (Liu et al. 2007).

DPP3 disrupt the KEAP1-Nrf2 complex by competing with Nrf2 about the KEAP1 binding site (Hast et al. 2013). This disruption prevents NRF2 degradation and subsequently leads to translocalization of Nrf2 into the nucleus and ARE activation. Overexpression of DPP3 in neuroblastoma cells (Liu et al. 2007), in HEK293T cells (Hast et al. 2013) or in MCF7 breast cancer cells (Lu et al. 2017) activates Nrf2-mediated transcription. Active and inactive variants of DPP3 were overexpressed in MCF7 cells and showed the same regulatory effect on oxidative stress (Lu et al. 2017). Hast et al. (2013) also showed a loss-of-function effect: silencing of DPP3 using specific siRNA Nrf2-mediated transcription was decreased down to levels of Nrf2-silencing.

Although DPP3 is known as an intracellular protein, DPP3 activity was detected in some bodily fluids as well: retroplacental serum (Shimamori et al. 1986), seminal plasma (Vanha-Perttula et al. 1988) and CSF (Aoyagi et al. 1993). In CSF there were elevated DPP3 activity levels measured in patients suffering from Alzheimer's disease (AD, Aoyagi et al., 1993).

DPP3 is known for being expressed as membranous, intracellular or circulating DPP3.

DPP3 has been not only proposed as potential biomarker but also as potential therapeutic target due to its ability to cleave several bioactive peptides. Influenca A virus changes host DPP3 levels for own replication (cell culture studies, Meliopoulos et al. 2012). Enkephalin and/or angiotensin degrading enzymes in general, including DPP3, have a therapeutic potential as targets for treatment of pain, cardiovascular diseases (CVD) and cancer and the corresponding inhibitors as potential treatments of pain, mental illnesses and CVD (Khaket et al. 2012, Patel et al. 1993, Igic et al. 2007).

Inhibition of DPP3

The activity of DPP3 can be inhibited unspecifically by different general protease inhibitors (e.g. PMSF, TPCK), sulfhydryl reagents (e.g. pHMB, DTNB) and metal chelators (EDTA, o-phenantroline) (Abramić et al. 2000, EP 2949332).

DPP3 activity can be further inhibited specifically by different kinds of compounds: an endogenous DPP3-inhibitor is the peptide spinorphin. Several synthetic derivatives of spinorphin, e.g. tynorphin, have been produced and shown to inhibit DPP3 activity to varying extents (Yamamoto et al. 2000). Other published peptide inhibitors of DPP3 are propioxatin A and B (U.S. Pat. No. 4,804,676) and propioxatin A analogues (Inaoka et al. 1988).

DPP3 can also be inhibited by small molecules such as fluostatins and benzimidazol derivatives. Fluostatins A and B are antibiotics produced in *Streptomyces* sp. TA-3391 that are non-toxic and strongly inhibit DPP3 activity. So far, 20 different derivatives of benzimidazol have been synthesized and published (Agić et al., 2007; Rastija et al., 2015), of which the two compounds 1' and 4' show the strongest inhibitory effect (Agić et al., 2007). Several dipeptidyl hydroxamic acids have been shown to inhibit DPP3 activity as well (Cviteŭić et al., 2016).

Oxidative Stress

Oxidative stress reflects an imbalance between the systemic manifestation of reactive oxygen species (hereinafter ROS)/reactive nitrogen species (hereinafter RNS) and antioxidants in favour of excessive generation of free radicals. This process leads to the oxidation of biomolecules with consequent loss of its biological functions and/or homeostatic imbalances, whose manifestation is the potential oxidative damage to cells and tissues. Accumulation of ROS/RNS can result in a number of deleterious effects such as lipid peroxidation, protein oxidation and DNA damage (including base damage and strand breaks). Further, some reactive oxidative species act as cellular messengers in redox signalling. Thus, oxidative stress can cause disruptions in normal mechanisms of cellular signalling.

"ROS" and "RNS" are the terms collectively describing free radicals and other non-radical reactive derivatives, which are also called oxidants. Radicals are less stable than non-radical species, although their reactivity is generally stronger. A molecule with one or more unpaired electron in its outer shell is called a free radical. Free radicals are formed from molecules via the breakage of a chemical bond such that each fragment keeps one electron, by cleavage of a radical to give another radical and, also via redox reactions. Free radicals related to oxidative stress include hydroxyl (OH.), superoxide ($O_2.^-$), nitric oxide (NO.), nitrogen dioxide ($NO_2$.), peroxyl (ROO.) and lipid peroxyl (LOO.). Also, hydrogen peroxide ($HNO_2$), ozone ($O_3$), singlet oxygen ($^1O_2$), hypochlorous acid (HOCl), nitrous acid ($HNO_2$), peroxynitrite ($ONOO^-$), dinitrogen trioxide ($N_2O_3$), lipid peroxide (LOOH), are not free radicals and generally called oxidants, but can easily lead to free radical reactions in living organisms.

Formation of ROS and RNS can occur in the cells by two ways: enzymatic and non-enzymatic reactions. Enzymatic reactions generating free radicals include those involved in the respiratory chain, the phagocytosis, the prostaglandin synthesis and the cytochrome P450 system. Free radicals can be produced from non-enzymatic reactions of oxygen with organic compounds as well as those initiated by ionizing radiations. The non-enzymatic process can also occur during oxidative phosphorylation (i.e. aerobic respiration) in the mitochondria. For a review see Pham-Huy et al. 2008. Int J Biomed Sci 4 (2): 89-96.

Diseases Associated with Oxidative Stress

In view of the stated above and with the context of the present invention, oxidative stress islinked to a number of diseases, including but not limited to neurodegenerative diseases, metabolic syndrome, cardiovascular disorders, autoimmune diseases, inflammatory lung diseases, kidney diseases, liver diseases, digestive diseases, viral infectious diseases, cancer and inflammation, and thus associated therewith.

According to the prior art, intracellular DPP3 is known to be closely linked to oxidative stress regulation. DPP3 was identified as an activator of the antioxidant response element (ARE) in an unbiased screen of a cDNA library consisting of approximately 15,000 full-length human expression cDNAs (Liu et al. 2007; see also above). ARE regulates the expression of a number of cytoprotective antioxidant enzymes and scavengers, contributing to endogenous defence against oxidative stress. This antioxidant effect of DPP3 is due to the interference of DPP3 with the KEAP1-Nrf2 signalling pathway. Nrf2 is a transcription factor that controls the basal and induced expression of an array of antioxidant response element-dependent genes to regulate the physiological and pathophysiological outcomes of oxidant exposure. Under normal or unstressed conditions, Nrf2 is bound to Kelch like-ECH-associated protein 1 (KEAP1) via its ETGE and its DLG motif. Within this protein cluster Nrf2 is kept in the cytoplasm, quickly ubiquinated and degraded by proteasome. Under oxidative stress, Nrf2 is not degraded, but instead translocates to the nucleus where it binds to a DNA promoter and induces expression of an array of antioxidant response element (ARE)—dependent genes. A variety of chemicals, including phytochemicals and derivatives (CDDO, sulforaphane), therapeutics (oltipraz, auranofin), environmental agents (paraquat, arsenic), and endogenous chemicals [NO, 15d-PGJ2, nitro-fatty acids, and 4-hydroxynonenal (4-HNE)], induce ARE genes through Nrf2 (Ma 2013).

BRIEF DESCRIPTION OF THE INVENTION

In view of the stated above, the inventors surprisingly and unexpectedly found that oxidative stress can be also reduced or regulated by a binder directed to and binding to a DPP3 protein or functional derivative thereof.

The inventors also found that oxidative stress can be also reduced or regulated by a binder directed to and binding to an epitope of SEQ ID NO.: 2, wherein the epitope is comprised in the DPP3 protein.

Moreover, the present inventors found a dipeptidyl peptidase 3 (hereinafter DPP3) binder directed to and binding to an epitope according to SEQ ID NO.: 2, wherein said epitope is comprised in a DPP3 protein or a functional derivative thereof, and wherein said DPP3 binder recognizes and binds to at least three amino acids (aa), preferably at least 4 aa of SEQ ID NO.: 2.

In the above context, the inventors specifically found that oxidative stress may be reduced or regulated by an anti-DPP3 antibody or an anti DPP3-antibody fragment directed to and binding to an epitope according to SEQ ID NO.: 2, wherein said epitope is comprised in a DPP3 protein or a functional derivative thereof, and wherein said DPP3 binder recognizes and binds to at least three amino acids (aa), preferably at least 4 aa of SEQ ID NO.: 2 or an anti-DPP3 non-Ig scaffold directed to and binding to an epitope according to SEQ ID NO.: 2, wherein said epitope is comprised in a DPP3 protein or a functional derivative thereof, and wherein said DPP3 binder recognizes and binds to at least three amino acids (aa), preferably at least 4 aa of SEQ ID NO.: 2.

Thus, the present invention provides the herein disclosed binder, and anti-DPP3 antibody or an anti-DPP3 antibody fragment binding to DPP3 or an anti-DPP3 non-Ig scaffold binding to DPP3 for use in methods of the preventive treatment or treatment of diseases or acute conditions of a patient, whereby said disease or acute condition is associated with oxidative stress.

Moreover, with the herein provided binder, DPP3 binder, and specifically the anti-DPP3 antibody, or anti DPP3-antibody fragment binding to DPP3 or an anti-DPP3 non-Ig scaffold binding to DPP3, the inventors have found binder to DPP3 which rapidly reduce or regulate oxidative stress in cells of a mammal when determined by the methods of respective biomarker measurements as further set out below.

Another subject of the present invention is a pharmaceutical composition comprising the binder of the invention, DPP3 binder of the invention, and specifically comprising the anti-DPP3 antibody or an anti-DPP3 antibody fragment binding to DPP3 or an anti-DPP3 non-Ig scaffold binding to DPP3 of the invention for use in methods of the prevention or treatment of diseases or acute conditions of a patient, whereby said disease or acute condition is associated with oxidative stress.

Hence, the herein disclosed pharmaceutical compositions are also provided for use in the prevention or treatment of symptoms, or syndromes, or pathological and acute conditions and disease associated problems, which are mediated by oxidative stress.

Diseases Associated with Oxidative Stress

As mentioned above, the occurrence of oxidative stress is linked to a number of diseases or disorders, which in accordance of the invention include:

neurodegenerative diseases, wherein said neurodegenerative diseases may be selected from a group comprising Alzheimer's disease (AD), Parkinson's disease (PD), Huntington's disease (HD), amyotrophic lateral sclerosis (ALS) and multiple sclerosis (MS)), metabolic syndrome, wherein said metabolic syndrome may be selected from a group comprising insulin resistance, obesity, hyperglycemia, dyslipidemia, hypertension and diabetes, cardiovascular disorders, wherein said cardiovascular disorders may be selected from a group comprising atherosclerosis, hypertension, heart failure, cardiovascular ischemia, cerebral ischemic injury, stroke and myocardial infarction, autoimmune diseases, wherein said autoimmune diseases may be selected from a group comprising rheumatoid arthritis, systemic lupus erythematosus, inflammatory lung diseases, wherein said inflammatory lung diseases may be selected from a group comprising COPD, asthma, kidney diseases wherein said kidney diseases may be selected from a group comprising renal toxicity (drug-induced kidney disease), acute kidney injury (AKI), chronic kidney disease (CKD), diabetic nephropathy, end-stage renal disease (ESRD), liver diseases wherein said liver diseases may be selected from a group comprising hepatotoxicity, viral hepatitis, cirrhosis, digestive diseases wherein said digestive diseases may be selected from a group comprising inflammatory bowel disease e.g. Ulcerative colitis, Crohn's disease, gastritis, pancreatitis and peptic ulcer, viral infectious diseases wherein said viral infectious diseases may be selected from a group comprising blood-borne hepatitis viruses (B, C, and D), human immunodeficiency virus (HIV), influenza A, Epstein-Barr virus, respiratory syncytial virus, cancer, wherein said cancer may be selected from a group comprising prostate cancer, breast cancer, lung cancer, colorectal cancer, bladder cancer, ovarian cancer, skin cancer, stomach cancer, liver cancer, and inflammation, and sepsis, septic shock, and SIRS.

In view of the stated above and with the context of the present invention, a detailed list of diseases and their association with oxidative stress is depicted in Table 1 below:

TABLE 1

The association of oxidative stress with diseases in accordance with the invention

| Disease group | Diseases | Reference |
| --- | --- | --- |
| Neurodegenerative disorders | Alzheimer's disease (AD), Parkinson's disease (PD), Huntington's disease (HD), amyotrophic lateral sclerosis (ALS) | Liu et al. 2017; Manoharan et al. 2016 |
|  | Multiple sclerosis (MS) | Adamczyk and Adamczyk-Sowa 2016 |
| Metabolic Syndrome | Insulin resistance, obesity, hyperglycemia, dyslipidemia, hypertension | Hutcheson and Rocic 2012 |
|  | Diabetes | Pitocco et al. 2013; Ullah et al. 2016 |
| Cardiovascular disorders | aterosclerosis, hypertension, heart failure, cardiovascular ischemia | Elahi et al. 2009 |
|  | heart failure | Tsutsui et al. 2011 |
|  | cerebral ischemic injury/stroke | Chen et al. 2011 |
|  | myocardial infarction | Hori and Nishida 2009 |
| Autoimmune disease | rheumatoid arthritis | Quiñonez-Flores et al. 2016 |
|  | systemic lupus erythematosus | Perl 2013 |
| Inflammatory lung disease | COPD, asthma | Holguin 2013 |
| Kidney disease | renal toxicity (drug-induced kidney disease) | Hosohata 2016; Naughton 2008 |
|  | acute kidney injury (AKI), chronic kidney disease (CKD), diabetic nephropathy, end-stage renal disease (ESRD) | Sureshbabu et al. 2015 |
| Liver diseases | Hepatotoxicity (drug-induced, alcohol-induced) | Li et al. 2015 |
|  | Viral Hepatitis | Ivanov et al. 2017 |
|  | Cirrhosis | Vairappan 2015 |

TABLE 1-continued

The association of oxidative stress with diseases in accordance with the invention

| Disease group | Diseases | Reference |
| --- | --- | --- |
| Digestive diseases | Inflammatory bowel disease e.g. Ulcerative colitis, Crohn's disease Gastritis, Pancreatitis, Peptic ulcer | Tian et al. 2017; Bhattacharyya et al. 2014 Bhattacharyya et al. 2014 |
| Viral infectious diseases | blood-borne hepatitis viruses (B, C, and D), human immunodeficiency virus(HIV), influenza A, Epstein-Barr virus, respiratory syncytial virus | Pohanka 2013; Schwarz 1996 |
| Cancer | general cancer | Sosa et al. 2013; Kruk and Aboul-Enein 2017 |
| | prostate cancer | Khandrika et al. 2009 |
| | breast cancer | Nourazarian et al. 2014 |
| | lung cancer | Valavanidis et al. 2013 |
| | colorectal cancer | Perse 2013 |
| | bladder cancer | Sawicka et al. 2015 |
| | ovarian, endometrial, cervical cancer | Saed et al. 2017 |
| | skin cancer | Narendhirakannan 2013 |
| | gastric cancer | Ma et al. 2013 |
| | liver cancer | Wang et al. 2013 |
| | leukemia | Kruk and Aboul-Enein 2017 |
| Inflammation/sepsis, septic shock, SIRS | sepsis | Kaymak et al. 2011 |

In more detail:

Oxidative stress is suspected to be important in neurological and neurodegenerative disorders including Amyotrophic lateral sclerosis (ALS), Parkinson's disease, Alzheimer's disease, Huntington's disease, Depression, Multiple sclerosis, tardive dyskinesia (TD), epilepsy and acute diseases of the central nervous system, such as spinal cord injuries and/or brain traumatic. The human brain is vulnerable to oxidative stress due to many facts such as (i) metabolism of catecholamines; (ii) decrease in antioxidants; (iii) presence of transition metals; (iv) occurrence of brain trauma/injury; and also (v) the brain is an organ that proportionally requires more oxygen and (vi) expresses low levels of antioxidant enzymes, which contribute to formation of ROS. As a consequence of redox unbalance in brain, one of the most affected structures is the lipid membrane (Rao and Balachandran 2002. Nutritional Neuroscience 5: 291-309). A common feature of these diseases is oxidative damage of neurons, which might be responsible for the dysfunction or death of neuronal cells that contributes to disease pathogenesis.

Alzheimer's disease (AD), the most prevalent neurodegenerative disorder, is characterized by the progressive deterioration of behaviour, cognition and functionality, which significantly impairs daily living activities. Numerous experimental and clinical studies have demonstrated that oxidative damage plays a key role in the loss of neurons and the progression to dementia in Alzheimer's disease. The production of β-amyloid (A(3), a toxic peptide often found in Alzheimer's patients' brain, is due to oxidative stress and plays an important role in the neurodegenerative processes. In addition, AB proteins can directly initiate free radical formation via the activation of NADPH oxidase. Moreover, inflammation is responsible for increased expression of cytokines, ROS levels, and cellular toxicity, thereby exacerbating AD progression. For review see Liu et al. 2017. *Oxidative Medicine and Cellular Longevity* 2525967; Manoharan et al. 2016. Oxid Med Cell Longev 8590578.

Huntington's disease (HD) is a progressive neurodegenerative disease linked with unstable expansion of cytosine, adenine, guanine (CAG) repeats in the HTT gene. The expansion of CAG repeats within the exon1 of the HTT gene gives rise to a mutation that leads to the elongation of polyglutamine tract, resulting in an HTT protein product that is susceptible to aggregation. The mHTT aggregates are accumulated throughout the brain of the affected individuals, which can interrupt protein quality control and transcription process. Those alterations are potentially responsible for the aberrant motor and cognitive problems in HD. Though oxidative damage is not much reported in the early stages of HD, it is proposed as one of the major mechanisms in HD as it progresses. Elevated oxidative stress plays a critical role in the late stage of HD pathogenesis. Impairment in the electron transport chain and mitochondrial dysfunction are the major mechanisms involved in the ROS mediated etiopathogenesis of HD. Dysfunction in the oxidative phosphorylation components has been documented in the brain tissues of HD patients. HD patients showed an increased level of oxidative stress markers accompanied by a decrease in antioxidant status compared to healthy subjects. For review see Liu et al. 2017. *Oxidative Medicine and Cellular Longevity* 2525967; Manoharan et al. 2016. *Oxid Med Cell Longev* 8590578.

Parkinson's disease (PD), the most common neurodegenerative disease of the elderly, is characterized by progressive loss of muscle control. PD is predominant at the $6^{th}$ decade of life and men are 1.5 to 2 times more likely to contract the disease than women. Head trauma, illness, or exposure to environmental toxins is identified as a risk factor. This neurodegenerative disorder is characterized by tremor, rigidity, bradykinesia, and impairment in balance. PD also causes cognitive, psychiatric, autonomic, and sensory disturbances. The pathology of PD is characterized by the gradual and selective loss of dopaminergic neurons in the substantia nigra pars compacta. Imbalance in dopamine metabolism due to oxidative stress has been recognised as a contributor to this disease. The major pathological findings include the presence of Lewy bodies in the substantia nigra and loss of nerve cells in the portions of its ventral tier. Several studies have reported impaired respiratory chain and somatic mitochondrial DNA mutations in the brain of patients with PD, which suggests the extensive role of oxidative metabolism in PD. Enhanced dopamine metabolism in the brain of patients with PD could account for the accumulation of toxic radicals such as hydroxyl in the brain. Iron accumulation in the neurons in the redox active form plays a crucial role in pathogenesis of this disease. Accumulation of iron has been reported in the substantia nigra in patients diagnosed with PD, which suggests the critical role of iron-induced lipid peroxidation in pathogenesis of PD A twofold increase in protein oxidation has been shown in the substantia nigra of PD patients compared to healthy subjects. Accumulation of hydroxyl radical due to lowered glutathione content in the brain has been reported in PD patients. Lowered activities of antioxidant enzymes and non-enzymatic antioxidants could be responsible for the progression of PD. For review see Liu et al. 2017. *Oxidative Medicine and Cellular Longevity* 2525967; Manoharan et al. 2016. *Oxid Med Cell Longev* 8590578.

Amyotrophic lateral sclerosis (ALS) is characterized by progressive loss of motor neurons in the anterior horn of the spinal cord. It is classified as either familial or sporadic depending on whether there is a clearly defined, inherited genetic element. Sporadic ALS (sALS) typically emerges between 50 and 60 years old. The onset of sALS is unknown, and thus the identification of causal genes and environmental factors remains elusive. In familial ALS, about 20% of the cases resulted from mutations in SOD1. The functions of SOD1 are diverse and include scavenging excessive superoxide radical, modulating cellular respiration, energy metabolism, and posttranslational modification. SOD dysfunction leads to a loss of antioxidant capability. Moreover, increased levels of ROS and ROS-associated damage have been widely reported in ALS. Increased markers of ROS damage have been found in biofluids of patients with sporadic ALS as well as in post-mortem tissue. For review see Liu et al. 2017. *Oxidative Medicine and Cellular Longevity* 2525967.

Multiple sclerosis (MS) is a multifactorial disease of the central nervous system (CNS) in which both inflammatory and neurodegenerative processes occur simultaneously. In the course of the disease inflammation is decreased whereas the degeneration of the CNS progresses. The inflammatory component in MS is important not only due to axonal and neuronal loss but also due to the fact that it starts the degenerative cascade in the early stage of MS. The induction of the activation of microglia and mitochondrial dysfunction plays a particular role in inflammatory processes. Microglia activated by T-lymphocytes release proteolytic enzymes, cytokines, oxidative products, and free radicals. It is also important that mitochondrial dysfunction results in an increased production of reactive oxygen species (ROS), which is detrimental to neurons and glia. On the other hand, oxidative stress damages the mitochondria, which disrupts the transport of adenosine triphosphate along the axon, and consequently leads to neurodegeneration. Oxidative stress is associated with the dysregulation of axonal bioenergetics, cytokine-induced synaptic hyperexcitability, abnormal iron accumulation, and the oxidant/antioxidant balance. Markers of oxidative stress assessed in the serum, erythrocytes CSF, saliva, and urine may have diagnostic properties whereas antioxidants may have clinical application in the future. For review see Adamczyk and Adamczyk-Sowa 2016. *Oxidative Medicine and Cellular Longevity* 1973834.

Oxidative stress is related to metabolic syndrome and its individual component pathologies, e.g. obesity, insulin resistance, dyslipidemia, impaired glucose tolerance and high blood pressure. The metabolic syndrome was defined by the World Health Organization criteria (Alberti and Zimmet 1998. *Diabet Med.* 15:539-553; *World Health Organization.* 1999. *Definition, diagnosis and classification of diabetes mellitus and its complications: report of a WHO Consultation. Part* 1: *diagnosis and classification of diabetes mellitus. Geneva, Switzerland: World Health Organization*) that require the presence of insulin resistance identified by one of the following: (1) type II diabetes; (2) impaired fasting glucose; (3) impaired glucose tolerance or (4) for those with normal fasting glucose levels (<110 mg/dL), glucose uptake below the lowest quartile for background population under investigation under hyperinsulemic, euglycemic conditions, AND two of the following: (1) blood pressure: ≥140/90 mmHg; (2) dyslipidemia: triglycerides (TG): ≥1.695 mmol/L and high-density lipoprotein cholesterol (HDL-C) ≤0.9 mmol/L (male), ≤1.0 mmol/L (female); (3) central obesity: waist:hip ratio>0.90 (male); >0.85 (female), or body mass index>30 kg/m$^2$; (4) microalbuminuria: urinary albumin excretion ratio≥20 µg/min or albumin:creatinine ratio≥30 mg/g.

Increased oxidative stress has emerged as playing a central role in metabolic syndrome and its component pathologies and may be a unifying factor in the progression of this disease. Moreover, oxidative stress has been identified as a major mechanism of micro- and macrovascular complications in the metabolic syndrome. For review see *Hutcheson and Rocic* 2012. *Exp Diabetes Res.* 2012:271028.

There is a bulk of evidence demonstrating that mitochondrial ROS (predominantly superoxide anion) overproduction is involved in diabetes and diabetic complications. It was suggested that glucose can directly stimulate ROS overproduction, and it was also shown that high glucose (HG) activates various enzymatic cascades in mitochondria, including activation of NADPH oxidase, uncoupling of NO synthases and stimulation of xanthine oxidase. Glycated proteins can also be the promoters of ROS formation, thus suggesting that different sources may be responsible for ROS overproduction and oxidative stress in diabetes. For review see Pitocco et al. 2013. *Int. J. Mol. Sci.* 2013, 14, 21525-21550.

Moreover, oxidative stress plays an important role in the pathogenesis and development of cardiovascular diseases, including hypertension, dyslipidemia, atherosclerosis, myocardial infarction, angina pectoris, and heart failure (Elahi et al. 2009. *Oxidative Medicine and Cellular Longevity* 2(5): 259-269). One of the key concepts of free radical mediated pathogenesis of cardiovascular disease is endothelial dysfunction, whereby the regulation of vascular wall microenvironment is disrupted. ROS activity in the vessel wall, for example, is thought to contribute to the formation of oxidized LDL, a major contributor to the pathogenesis of atherosclerosis. Oxidative stress also plays a role in the ischemic cascade due to oxygen reperfusion injury following hypoxia. This cascade includes both stroke (Chen et al. 2011. *Antioxidants and Redox Signaling* 14(8): 1505-1517) and myocardial infarction (MI) (Hori and Nishida et al. 2009. *Cardiovascular Research* 81: 457-464). During brain ischemia/reperfusion, multiple detrimental processes take place, including overproduction of oxidants, inactivation of detoxification systems, and consumption of antioxidants. These changes cause the disruption of the normal antioxidative defense ability of brain tissue (Chen et al. 2011. *Antioxidants and Redox Signaling* 14(8): 1505-1517). For further review see Elahi et al. 2009. *Oxidative Medicine and Cellular Longevity* 2(5): 259-269.

A number of experimental and clinical studies have demonstrated the increased generation of ROS in heart failure (HF) and showed that oxidative stress is involved in the pathophysiology of HF in the heart as well as in the skeletal muscle. The high metabolic activity of the mitochondria-rich myocardium makes these findings seem intuitively obvious. Oxidative stress clearly activates processes in isolated heart cells such as changes in gene expression and cell death that are now accepted components of myocardial remodeling and heart failure. Moreover, many studies have been performed in animal models that demonstrate therapeutic effects of antioxidants on progression of heart failure. For review see Tsutsui et al. 2011. *Am J Physiol Heart Circ Physiol* 301: H2181-H2190.

Excessive oxidative stress is thought to have an important role in the pathogenesis of autoimmune diseases. Many studies have shown that T and B lymphocytes contribute to the pathogenesis of autoimmune diseases by the production of autoantibodies and ROS under environmental and genetic influence. Oxidative stress has been implicated in autoimmune disorders (rheumatoid arthritis, systemic lupus erythematosus, psoriasis, and celiac disease) where it plays an important role in the disease process. Oxidative stress is increased in systemic lupus erythematosus (SLE), and it contributes to immune system dysregulation, abnormal activation and processing of cell-death signals, autoantibody production and fatal comorbidities. Mitochondrial dysfunction in T cells promotes the release of highly diffusible inflammatory lipid hydroperoxides, which spread oxidative stress to other intracellular organelles and through the bloodstream. Oxidative modification of self antigens triggers autoimmunity, and the degree of such modification of serum proteins shows striking correlation with disease activity and organ damage in SLE (Perl 2013. *Nat Rev Rheumatol.* 9(11): 674-686). Rheumatoid arthritis (RA) is an autoimmune disease characterized by chronic inflammation of the joints and tissue around the joints with infiltration of macrophages and activated T cells. The pathogenesis of this disease is due to the generation of ROS and RNS at the site of inflammation. RA is one of the conditions that induce oxidative stress. A fivefold increase in mitochondrial ROS production in whole blood and monocytes of RA patients—compared with healthy subjects suggests that oxidative stress is a pathogenic hallmark in RA. Free radicals are indirectly implicated in joint damage because they also play an important role as secondary messengers in inflammatory and immunological cellular response in RA. T-cell exposure to increased oxidative stress becomes refractory to several stimuli including those for growth and death and may perpetuate the abnormal immune response. On the other hand, free radicals can degrade directly the joint cartilage, attacking its proteoglycan and inhibiting its synthesis (for review see Quiñonez-Flores et al. 2016. *Biomed Res Int.* 2016:6097417).

There is now substantial evidence that inflammatory lung diseases such as asthma and chronic obstructive pulmonary disease (COPD) are characterized by systemic and local chronic inflammation and oxidative stress. An important source for increased airway oxidative stress is the recruitment of inflammatory cells into the airway after exposure to trigger factors. These activated cells can generate anion superoxide through reduced nicotinamide adenine dinucleotide phosphate (NADPH) oxidase pathway. Mitochondrial dysfunction in airway epithelial cells, which occurs in response to mechanical and environmental stimuli, can also contribute to the formation of anion superoxide and airway oxidative stress. Subjects with asthma have greater systemic and airway increased oxidative stress, which is associated with worse asthma severity. As with asthma, subjects with COPD have increased airway oxidative stress and nitrosative stress. Patients with COPD have a greater degree of immunostaining for nitrotyrosine in the airway epithelium and inflammatory cells in sputumA significant imbalance in the airway thiol metabolism has also been described for patients with COPD, which may be associated with downstream redox transcription changes and proinflammatory events. For review see Holguin 2013. *Ann Am Thorac Soc* 10 Supplement: S150-S157.

Inflammatory bowel disease (IBD) is an incurable chronic inflammatory intestinal disorder of the gastrointestinal (GI) tract that dramatically impacts quality of life. Crohn's disease (CD) and ulcerative colitis (UC) are the principal types of IBD. CD may occur in any region of the GI tract involving the ileum and colon in a discontinuous pattern by transmural inflammation, while UC affects only the colon and rectum continuously and is restricted to the mucosa. Accumulating data from both experimental models and clinical studies indicate that oxidative stress signalling is involved in and contributes to the development of IBD through multiple levels of function. Oxidative stress leads to damages of the mucosal layer in the GI tract and bacterial invasion, which in turn stimulates the immune response and initiates IBD. During inflammation, immune cells, such as leukocytes, monocytes, and neutrophils augment ROS production during respiratory, prostaglandin, and leukotriene metabolism, resulting in further tissue damages. For review see Tian et al. 2017. *Oxid Med Cell Longev* 4535194.

Celiac disease (CD) is an immune-mediated chronic inflammatory disorder of the upper small intestine induced by gluten and related prolamines in genetically susceptible individuals. As in other autoimmune conditions, environmental, genetic, and immunological factors may be involved in the pathogenesis of CD. In addition to this, oxidative stress is also implicated in the pathogenesis of CD. For example, activation of xanthine oxidase is one of the mechanisms of ROS overproduction in small intestinal mucosa of celiac patients. For review see Patlevic et al. 2016. *Integr Med Res* 5: 250-258.

Gastritis is defined as inflammation of the stomach mucosal lining and occurs in several conditions including *H. pylori* infection, NSAID use, alcohol consumption, and stress. Peptic ulcer disease (PUD) occurs in the proximal GI tract and is often associated with chronic gastritis. Gastric and duodenal ulcers represent the most common and chronic PUDs. Gastritis and peptic ulcer are caused by multiple factors, both endogenous and exogenous, and free radicals are closely linked to both conditions. There are several factors contributing to the accumulation of ROS in the stomach. Reduced antioxidant enzyme SOD levels and antioxidant vitamin intake contribute to the accumulation of ROS associated with gastroduodenal inflammatory diseases. Ethanol-induced gastric inflammation is associated with increased superoxide generation. Phagocytic leukocytes are the main source of ROS in chronic inflammation such as one observes in *H. pylori* induced gastritis and IBD. Significant numbers of neutrophils and/or macrophages infiltrate the gastric mucosa during inflammation, generating large amounts of ROS. For review see Bhattacharyya et al. 2014. *Physiol Rev* 94: 329-354.

Oxidative stress also plays a critical role in liver diseases like viral Hepatitis (Type A, B and C) and liver cirrhosis. It has been clearly established that hepatitis C is associated with strong oxidative stress. This was revealed in liver tissues and in blood serum/plasma samples of Cchronic hepatitis C patients using a variety of techniques, including direct measurement of ROS, quantification of DNA, lipid and protein oxidation products, as well as by assessing the total oxidant/antioxidant status or the levels of individual antioxidants. Screening of the liver biopsies of chronic hepatitis C virus carriers revealed significant elevation of the levels of oxygen radicals and stress markers malondialdehyde (MDA) and 4-hydroxynonenal-(HNE)- and other protein adducts. In addition, serum/plasma of such patients is characterized by increased levels of a wide array of oxidative stress markers such as MDA, lipid peroxides, protein carbonyl content or thioredoxin (for review see Ivanov et al. 2017. *Oncotarget*, 2017, Vol. 8, (No. 3), pp: 3895-3932).

Patients with chronic hepatitis B exhibit signs of pronounced oxidative stress. Levels of oxygen radicals in liver specimens from these patients exceed the levels in healthy people. Patients with hepatitis B exhibit signs of oxidative stress not only in the liver but also in plasma/sera. Chronic hepatitis B is accompanied by an increase in total oxidant status and a concomitant reduction of total antioxidant status. Plasma/serum of these patients was also characterized by the elevated levels of ROS, including $H_2O_2$, and oxidation products of lipids and proteins. Oxidative stress is not just a hallmark of chronic HBV infection and advanced liver disease; it is also observed in acute and occult hepatitis B, as well as in asymptomatic HBV infections. Occult hepatitis B infection is characterized by increased levels of ROS in lymphocytes and consequent DNA damage. However, the most dramatic changes have been described in hepatitis B patients with liver cirrhosis and with acute chronic hepatitis B liver failure (for review see Ivanov et al. 2017. *Oncotarget*, 2017, Vol. 8, (No. 3), pp: 3895-3932).

Cirrhosis is a complication of many forms of chronic liver diseases and is a late stage of fibrosis, in which regenerative nodular formation surrounded by fibrous bands of the liver. In cirrhosis, oxidative stress induced mainly by an overproduction of reactive oxygen species, which is a critical determinant of endothelial dysfunction and is due to disturbed balance between oxidant and antioxidant enzymes. Increased superoxide formation in the presence of equimolar concentrations of NO will lead to the formation of the potent ROS and reactive nitrogen species. For review see Vairappan 2015. *World J Hepatol* 27; 7(3): 443-459.

Hepatotoxicity implies chemical-driven liver damage. Drug-induced liver injury is a cause of acute and chronic liver disease. Drug-induced liver injury is responsible for 5% of all hospital admissions and 50% of all acute liver failures. The liver is the most frequently targeted organ in terms of drug toxicity. The production of radical species, specifically ROS and RNS, has been proposed as an early event of drugs hepatotoxicity and as an indicator of hepatotoxic potential. It has been discovered that a lot of drugs could induce oxidative stress including increase of cellular oxidants and lipid peroxidation, depletion of antioxidants in the liver, such as anti-inflammation drugs, anti-analgesic drugs, anti-cancer drugs and antidepressants (Li et al. 2015. *Int. J. Mol. Sci.* 16: 26087-26124). More than 900 drugs have been implicated in causing liver injury, which are hereby incorporated by reference (https://livertox.nlm nih.gov/; Björnsson 2016. *Int. J. Mol. Sci.* 17: 224).

In the pathogenesis of alcoholic liver disease (ALD), the direct consequence of ethanol metabolism also seems to be related to ROS production, mitochondrial injury and steatosis, which are the common features of acute and chronic alcohol exposure (Li et al. 2015. *Int. J. Mol. Sci.* 16: 26087-26124).

Both acute kidney injury (AKI) and chronic kidney disease (CKD) that lead to diminished kidney function are interdependent risk factors for increased mortality. If untreated over time, end stage renal disease (ESRD) is an inevitable outcome. Acute and chronic kidney diseases occur partly due to imbalance between the molecular mechanisms that govern oxidative stress, inflammation, autophagy and cell death. Numerous studies suggest oxidative stress and its systemic effects play a pivotal role in the development of AKI. A recent study demonstrated an increased urinary thioredoxin 1 (TRX1) expression as an oxidative stress biomarker with respect to renal injury. Diabetic nephropathy (DN) is a devastating complication of diabetes and a major cause of CKD. In kidney, mitochondrial respiratory chain and NADPH oxidases (NOX) are the major common sources of ROS and NOX have been demonstrated to produce oxidative stress by enhancing vascular dysfunction and fibrosis in CKD. For review see Sureshbabu et al. 2015. *Redox Biology* 4: 208-214.

Drug-induced kidney injury (nephrotoxicity) is a serious problem in clinical practice and accounts for 19%-26% of cases with acute kidney injury (AKI) among hospitalized patients. Moreover, AKI causes a severe condition associated with high probabilities of developing progressive chronic kidney disease or end-stage renal disease, thus leading to high mortality rates. Most drugs found to cause nephrotoxicity exert toxic effects by one or more common pathogenic mechanisms. These include altered intraglomerular hemodynamics, tubular cell toxicity, inflammation, crystal nephropathy, rhabdomyolysis, and thrombotic microangiopathy. AKI includes acute tubular necrosis (ATN) and acute interstitial nephritis (AIN). A mechanism underlying ATN is oxidative stress. Proximal tubular toxicity develops due to direct nephrotoxic effects such as mitochondrial dysfunction, lysosomal hydrolase inhibition, phospholipid damage, and increased intracellular calcium concentration, leading to formation of reactive oxygen species (ROS) with injurious oxidative stress (Hosohata 2016. *Int. J. Mol. Sci.* 17: 1826).

Medications that are potentially harmful to the kidneys (nephrotoxic) are, e.g. antimicrobials like antibiotics (for example streptomycin, gentamicin) or antivirals (for example acyclovir, foscarnet) or antifungal (for example amphotecerin B), analgesics, non-steroidal anti-inflammatory drugs (NSAID) (for example ibuprofen, naproxen), diuretics, proton pump inhibitors, chemotherapeutics (for example cisplatin), contrast dyes, cardiovascular agents like ACE-inhibitors or statins, anti-depressants, immune suppressants (for example cyclosporine A) and antihistamines (for reference see Naughton 2008. *Am Fam Physician.* 2008; 78(6):743-750, Table 1; Hosohata 2016. *Int. J. Mol. Sci.* 17: 1826).

In carcinogenesis, high reactive hydroxyl radicals cause oxidative DNA damage and peroxynitrite, which causes both oxidative damage and nitration of DNA bases. The majority of mutations induced by ROS appear to involve guanine modification, causing guanine (G)→thymin (T) transversions. If it relates to critical genes such as oncogenes or tumor suppressor genes, initiation or progression of cancer can result. The high metabolism of cancer cells is generally associated with an increase in ROS; however, such levels are less deleterious in cancer cells than they would be in normal cells. For example, although the ROS level increases by a modest degree, tumorigenic cells can induce a new redox balance, resulting in cellular adaptation and proliferation. The ROS generated by the respiratory chain in the mitochondria and by the Nox enzymes in the cytoplasm are particularly important. In fact, Nox proteins are now considered to be oncogenic proteins, and mitochondrial dysfunction is associated with tumorigenesis. Oxidative stress is involved in all stages of carcinogenesis and there is a dose-dependent association between level of the persistent or chronic oxidative stress and the tumor stage. During the carcinogenesis process the normal cells are transformed into abnormal cells owing to a number of structural changes and mutations in genes expression. In the subject literature carcinogenesis is described by three main stages: initiation, promotion and progression. All these stages have been postulated to be linked with contribution of ROS and RNS. ROS have an important role in the pathophysiological states involved in neovascularization. For example ROS-generating enzymes, such as NADPH oxidases (e.g., Nox: Nox1-5), activate redox signaling pathways that ultimately lead to angiogenesis. For review see Kruk and Aboul-Einein 2017. *Mini-Reviews in Medicinal Chemistry* 17: 904-919; Sosa et al. 2013. *Ageing Research Reviews* 12: 376-390.

Prostate cancer is the most frequently diagnosed non-cutaneous malignancy in males. This is a multi-focal, filed-type disease, which forms solid tumors of glandular origin. Prostate cancer is mainly a disease of aging, with most cases occurring in men over the age of 55. Over the last decade association between prostate cancer risk and oxidative stress has been recognized, and epidemiological, experimental and clinical studies have unequivocally proven a role for oxidative stress in the development and progression of this disease, commonly associated with a shift in the antioxidant-prooxidant balance towards increased oxidative stress. Environmental factors like diet, inflammation, and changes in cellular functions pertaining to NAD(P)H Oxidase, androgen signalling, mitochondrial DNA mutations, aging, and redox imbalance are possible mechanisms that contribute to increase ROS generation. This increased ROS may further stimulate cell proliferation, cause somatic DNA mutations and promote genetic instability, cell cycle arrest, senescence, and in cancer cells can cause increased angiogenesis, and motility. Especially increased Nox expression driven ROS generation in prostate cancer could lead to the generation of a malignant phenotype by modulating various signalling cascades. For review see Khandrika et al. 2009. *Cancer Lett.* 282(2): 125-136; Kruk and Aboul-Einein 2017. *Mini-Reviews in Medicinal Chemistry* 17: 904-919; Sosa et al. 2013. *Ageing Research Reviews* 12: 376-390.

The excessive production of ROS in breast cancer cells include: a strong expression of thymine phosphorylase leading to degradation of thymidine to thymine and 2-deoxy-D-ribose phosphate; oxidation of 17-estradiol panoxyl radicals to lactoperoxidase participating in metabolism of estrogens and inflammation. In addition to the increase in free radicals, antioxidant changes are related to breast cancer risk, for example the levels of SOD and GPX were found to be higher in the blood of breast cancer cases compared to that of healthy women as a reply on the increased production of superoxide and hydrogen peroxide. In breast cancer, the tumor suppressor gene breast cancer gene 1 (BRCA1) is mutated in 40-50% of hereditary breast cancers and absent or expressed at low levels in 30-40% of sporadic breast cancers. BRCA1 is a caretaker gene that is responsible for repairing DNA, and it is able to upregulate several genes involved in the antioxidant response by controlling the activity of the transcription factors Nrf2 and NfKB. Apart from the inhibitory action of BRCA1 on ROS generation, BRCA1 also reduces the levels of protein nitration due to RNS accumulation in cells, and it enhances DNA repair processes that ultimately help to cope with oxidative stress. For review see Nourazarian et al. 2014 *Asian Pac J Cancer Prev,* 15 (12): 4745-4751; Kruk and Aboul-Einein 2017. *Mini-Reviews in Medicinal Chemistry* 17: 904-919; Sosa et al. 2013. *Ageing Research Reviews* 12: 376-390.

The human lungs are exposed continuously to air pollution oxidants in addition to endogenously generated ROS and RNS, which are involved in physiological biochemical mechanisms and normal cellular signalling pathways. It is a commonly considered hypothesis that tobacco smoking is a key risk factor in lung cancer development. Both, clinical and experimental research has consistently shown the important role of OS in lung cancer. Evidence is available that supports the importance of oxidative stress and its correlation with increased incidence of malignant respiratory diseases due to inflammation, activation of transcriptional factors and DNA damage. During inflammation, enhanced ROS production induces DNA damage, inhibition of apoptosis, and activation of protooncogenes by initiating signal transduction pathways. Inflammatory cells are particularly effective in generating ROS and other reactive species, thus increasing oxidative damage and promoting mechanisms of carcinogenesis. The ability of respirable particles or fibrous dusts to penetrate the respiratory system and reach the lung alveoli in order to generate ROS and other oxidants or free radicals is suggested to be the main factor involved in their pathogenic potential. Synergistic mechanisms of inhalable particulate matter (penetrating deep into the lung's alveoli) and other components of air pollution (ozone, nitric oxide, soot, heavy metals, PAHs) and tobacco smoke have been studied. The porous surfaces of airborne particles provide a fertile ground for catalyzing the increased generation of ROS or other damaging oxidants, which are potential initiators of pulmonary carcinogenesis. For review see Valavanidis et al. 2013. *Int. J. Environ. Res. Public Health* 10: 3886-3907; Kruk and Aboul-Einein 2017. *Mini-Reviews in Medicinal Chemistry* 17: 904-919; Sosa et al. 2013. *Ageing Research Reviews* 12: 376-390.

Colorectal cancer (CRC) is one of the most common cancers worldwide, with the highest incidence rates in western countries. Colon cancer originates from the epithelial cells that line the bowel. These cells divide rapidly and have a high metabolic rate, which has been found as a potential factor that may be responsible for increased oxidation of DNA. It was found that the human colorectal tumors (adenomasand carcinomas) have increased levels of different markers of oxidative stress, such as increased levels nitric oxide (NO), 8-oxodG in DNA, lipid peroxides, glutathione peroxidase (GPx), catalase (CAT), and decreased methylation of cytosine in DNA. Besides lipid modifications also increased leukocyte activation in carcinogenic tissue was found, which indicates possible contribution of inflammatory cells to a further oxidative stress. Moreover, it was shown that levels of anti-oxidant vitamins A, C, E in blood plasma of colorectal cancer patients were statistically lower compared to healthy individuals. For review see Perse 2013. *BioMed Research International* 725710; Kruk and Aboul-Einein 2017. *Mini-Reviews in Medicinal Chemistry* 17: 904-919; Sosa et al. 2013. *Ageing Research Reviews* 12: 376-390.

In the industrialized countries, bladder cancer is the fourth most frequently occurring malignant tumors. Recent studies indicate the involvement of oxidative and nitrosative stress in the formation and development of this disease. Red-ox disorders are characteristic for both, the initiation and progression of bladder cancer. There are observed changes in the activity of transcription factors, such as nuclear factor NF-kB; transcription factors: AP-1, Nrf2 and STATS and hypoxia-inducible factor HIF-1α. In addition, studies indicate a role for oxidative stress in the regulation of MAPK cascade and its involvement in carcinogenesis consisting bladder. Nitric oxide also plays an important role in tumor biology. Numerous studies show that the bladder cancer is characterized by an intensified production of NO. In contrast to the ROS, which overproduction result from exposure to carcinogenic xenobiotic, nitrogen oxide in high level is produced during inflammation. Sustained iNOS activity therefore plays an important role in carcinogenesis associated with the inflammatory response, characteristic also for bladder cancer. For review see Sawicka et al. 2015. *Postepy Hig Med Dosw* 69: 744-752.

Ovarian cancer is the fifth leading cause of cancer death; the leading cause of death from gynecologic malignancies, and the second most commonly diagnosed gynecologic malignancy. The overwhelming majority of ovarian cancers are derived from ovarian surface epithelium. Metastasis is achieved through detachment of single cells or clusters of cells from the primary tumor followed by implantation on peritoneal mesothelial lining Ovarian, endometrial, and cervical cancer consist a great problem in oncology due to their diagnosis in advanced stage. Research finding have shown that oxidative stress plays a causal role in the carcinogenesis of two subtypes of ovarian cancer: clear cell carcinoma and endometriosis carcinoma. Evidence suggests that ovarian cancer patients have decreased levels of circulating antioxidants and higher levels of oxidative stress. It has been reported that epithelial ovarian cancer (EOC) tissues and cells manifest a pro-oxidant state characterized by an increased expression of key pro-oxidant enzymes and decreased expression of antioxidant enzymes. Specifically, EOC cells and tissues manifested an increased expression of iNOS, MPO, NAD(P)H oxidase, as well as an increase in NO levels. Moreover, EOC cells manifested lower apoptosis.

Endometrial cancer has been reported to be associated with endometriosis disease, and the high levels of free iron hemosiderin or heme in endometrial cysts are considered as a main factor responsible for the oxidative stress development and chronic inflammation.

Cervical cancer is the second most common cancer in women worldwide being a subject of intensive research. Several experimental studies suggested the participation of oxidative stress in cervical, indicating that antioxidants can alter the redox balance in cervical cancer cells, inhibit transcription factors AP-1 and NF-κB or induce cell apoptosis. For review see Saed et al. 2017. *Gynecologic Oncology* 145: 595-602; Kruk and Aboul-Einein 2017. *Mini-Reviews in Medicinal Chemistry* 17: 904-919; Sosa et al. 2013. *Ageing Research Reviews* 12: 376-390.

Oxidative damage induced by OS has been also implicated in leukemia and the decreased levels of antioxidants and oxidatively modified DNA and lipids caused by high ROS production were found in serum of chronic lymphocytic leukemia patients. Moreover, it was found that the chronic leukemia cells were able to adapt to intracellular OS through upregulation the stress-responsive hemeoxygenase-1 confirming involvement of ROS in the pathogenesis of leukemia cancer. Also, GSH depletion in lymphocytes of the chronic lymphocytic has been demonstrated in leukemia B patients. For review see Kruk and Aboul-Einein 2017. *Mini-Reviews in Medicinal Chemistry* 17: 904-919.

Gastric cancer (GC) is one of the most frequent diseases in human population. It is the fourth frequent cancer and the second most common cause of deaths from cancer in the world. The main risk factor for gastric cancer is chronic inflammation caused by bacterial growth. For example, infection by *Helicobacter pylori*, which increases the production of reactive oxygen and nitrogen species in human stomach, is thought to be important in the development of gastric cancer. It has been shown that protein oxidation products were significantly higher in GC patients. Moreover, it was found that the antioxidant potentials of SOD and catalase were lower in gastric cancer tissues compared to the control healthy tissues. For review see Kruk and Aboul-Einein 2017. *Mini-Reviews in Medicinal Chemistry* 17: 904-919; Ma et al. 2013. *Oxidative Medicine and Cellular Longevity* 543760.

There are many factors involved in liver carcinogenesis, including hepatitis B virus (HBV) and hepatitis C virus (HCV) infection, alcohol abuse, and nonalcoholic fatty liver disease (NAFLD), aflatoxin B 1, obesity, diabetes, dietary habits, and iron accumulation. In general, oxidative stress can be triggered by any dangerous or inflammatory signal and affects multiple cells in the liver. Liver injury can be either an acute or a chronic inflammatory process. In the environment of local inflammation, many types of liver cells, such as liver sinusoidal endothelial cells (LSECs), hepatic stellate cells (HSCs), dendritic cells (DCs), and Kupffer cells (KCs), are activated. These cells produce many kinds of immune mediators, cytokines, and chemokines that may also lead to the production of oxidative stress. In recent years, studies on the relationship between oxidative stress and hepatic stellate cells have been increasing. These cells have been proven to play a central part in the process of liver fibrosis and can induce collagen production after activation in the body by free radicals, which are produced by ROS and superoxide anions, and further induce damage to liver cells.

It is known that over 80% of cases of HCC are associated with chronic HBV or HCV infection. HBV- and HCV-related chronic inflammation and fibrosis of the liver are usually induced by oxidative stress, which contributes to the pathogenesis of hepatocarcinogenesis. HBV infection results in activation of macrophages to produce a variety of proinflammatory cytokines, such as IL-1β, IL-6, CXCL-8, and TNF-α. Such persistent abnormal production of cytokines and the resulting production of ROS have an influence on hepatocarcinogenesis. HCV-induced oxidative stress contributes to the development of hepatocellular carcinoma (HCC). Moreover, levels of oxidative stress markers in chronic hepatitis C patients correlate positively with the probability of development of HCC and can serve as prognostic markers for HCC recurrence in chronic hepatitis C patients who underwent liver transplantation. Carcinogenesis is orchestrated by multiple ROS-mediated processes. For review see Wang et al. 2016. *Oxidative Medicine and Cellular Longevity* 7891574.

Skin is a major environmental interface for the body, which accidentally or occupationally gets exposed to a number of chemical mutagens and carcinogens. Skin cancer represents a major and growing public health problem. It accounts for more than 40% of all new cancer diagnosed. 80% of skin cancers result from basal cell carcinomas (BCC); another 16% are squamous cell carcinomas (SCC), and 4% are melanomas. A large number of evidence indicates that UV can induce DNA damage and as a consequence DNA strand breaks and DNA cross links are detected. An important process in skin cancer is generation of hydrogen peroxide by melanocytes and decrease in catalase activity. Moreover, there are findings showing that mutations in several genes linked with melanoma result from oxidative stress. For review see Kruk and Aboul-Einein 2017. *Mini-Reviews in Medicinal Chemistry* 17: 904-919; Narendhirakannan. 2013. *Ind J Clin Biochem* 28(2):110-115.

Reactive species generated during infection may have serious consequences for the disease once they are released to any degree. The oxidative stress can initiate adverse effects in different organs. Development of oxidative stress can be accelerated in the course of hypoxia. Hypoxia is a known complication of infectious diseases. Hypoxia is not peculiar to one disease. Influenza, viral hepatitis and tuberculosis are all examples of infectious diseases in which hypoxia takes place. Direct generation of reactive oxygen species can be initiated by metals. In an example, iron, cooper, and cadmium can catalyze the development of oxidative stress by Fenton reaction in which hydrogen peroxide is converted into hydroxyl radical and hydroxide anion. Heavy metals are involved in pathological processes linked to infections like other pathologies. As mentioned, livers damaged by viral hepatitis are vulnerable to heavy metals due to faulty elimination processes. Clinical studies on patients with viral hepatitis A, B, C, D, and E demonstrated that accumulation of copper and iron caused oxidative stress and oxidative damage to patients' liver tissue. Like hepatitis, AIDS is accompanied by imbalance in oxidative homeostasis. Elevated markers of oxidative damage of targets in the body and accumulation of reactive oxygen species are common in HIV-infected patients. Blood antioxidants are reduced over the long term in the infected individuals. For review see Pohanka 2013. *Folia Microbiol* 58:503-513.

Sepsis and septic shock remain as leading cause of death in adult intensive care units. It is widely accepted that sepsis and septic shock are caused predominantly by gram-negative bacteria and their endotoxins. Endotoxin or Lipopolysaccharide (LPS) have important roles as host responses and trigger the inflammatory processes, caused by gram-negative bacterial infection. Production of oxygen radicals by neutrophils and macrophages such as reactive oxygen species (ROS), NO (nitric oxide) and peroxynitrite promote gene expression of proinflammatory mediators. ROS and RNS are antimicrobial agents produced by these leukocytes that can directly destroy microbial pathogens. During sepsis, excess production of ROS and RNS threatens the integrity of various biomolecules including proteins, lipids as well as lipoproteins, protein oxidation and DNA resulting in tissue damage, by lipid peroxidation of cell membranes, protein oxidation and DNA strand breaks. These mechanisms contribute to multi organ failure during sepsis resulting in myocardial depression, hepatocellular dysfunction, endothelial dysfunction, and vascular catecholamine hypo-responsiveness. As a major source of ROS production, mitochondria are especially prone to ROS-mediated damage. Such damage can induce the mitochondrial permeability transition caused by opening of nonspecific high conductance permeability transition pores in the mitochondrial inner membrane. ROS themselves also provide a signal leading to the induction of autophagy, apoptosis, and necrosis. Excessive ROS production and adenosine triphosphate depletion from uncoupling of oxidative phosphorylation promote necrotic cell death. Release of cytochrome-c after mitochondrial swelling activates caspases and initiates apoptotic cell death. For review see Kaymak et al. 2011. *FABAD J. Pharm. Sci.* 36: 41-47.

Thus, in another specific embodiment of the invention the herein disclosed DPP3 binder, specifically the herein provided anti-DDP3 antibody, and/or an anti-DPP3 antibody fragment or an anti-DPP3 non-Ig scaffold which are binding to an epitope according to SEQ ID NO.: 2, which is comprised in a DPP3 protein or a functional derivative thereof are provided for the use in the prevention or treatment of a disease or acute condition of a patient, whereby said disease or acute condition is associated with oxidative stress, said disease is selected from the group comprising the above described neurodegenerative diseases, metabolic syndrome, cardiovascular disorders, autoimmune diseases, inflammatory lung diseases, kidney diseases, liver diseases, digestive diseases, viral infectious diseases, cancer, inflammation, sepsis, septic shock and SIRS.

In another specific embodiment said disease is selected from the group comprising neurodegenerative diseases (e.g. Alzheimer's disease (AD), Parkinson's disease (PD), Huntington's disease (HD), amyotrophic lateral sclerosis (ALS) and multiple sclerosis (MS)), metabolic syndrome (including insulin resistance, obesity, hyperglycemia, dyslipidemia, hypertension and diabetes), cardiovascular disorders (e.g. atherosclerosis, hypertension, heart failure, cardiovascular ischemia, cerebral ischemic injury/stroke and myocardial infarction), autoimmune diseases (e.g. rheumatoid arthritis and systemic lupus erythematosus), inflammatory lung diseases (e.g. COPD, asthma), kidney diseases (including renal toxicity (drug-induced kidney disease), acute kidney injury (AKI), chronic kidney disease (CKD), diabetic nephropathy, end-stage renal disease (ESRD)), liver diseases (e.g. hepatotoxicity, viral hepatitis, cirrhosis), digestive diseases (including inflammatory bowel disease e.g. Ulcerative colitis, Crohn's disease; gastritis, pancreatitis and peptic ulcer), viral infectious diseases (e.g. blood-borne hepatitis viruses (B, C, and D), human immunodeficiency virus (HIV), influenza A, Epstein-Barr virus, respiratory syncytial virus)), cancer (e.g. prostate cancer, breast cancer, lung cancer, colorectal cancer, bladder cancer, ovarian cancer, skin cancer, stomach cancer, liver cancer) and inflammation, sepsis, septic shock and SIRS.

In another specific embodiment of the invention the herein disclosed DPP3 binder, specifically the herein provided anti-DDP3 antibody, and/or an anti-DPP3 antibody fragment or an anti-DPP3 non-Ig scaffold which are binding to an epitope according to SEQ ID NO.: 2, which is comprised in a DPP3 protein or a functional derivative thereof are provided for the use in the prevention or treatment of an acute condition, wherein said acute condition may be selected from a group comprising hepatotoxicity and kidney toxicity.

Toxicities Resultant from Alcohol Consumption, Chronic Exposure to Cigarette Smoke and as a Side-Effect of Different Drug Treatments In the context of the present invention, oxidative stress and subsequent toxicities can also be induced by chronic alcohol consumption, chronic exposure to cigarette smoke and as a side-effect of different drug treatments (reviewed in Deavall et al. 2012, see table 2 below).

Acetaminophen—a widely used analgesic and antipyretic drug—is a prototypical hepatotoxicant for drug-induced liver injury that is connected to KEAP-Nrf2 signaling (Ma, 2013). Other therapeutics inducing oxidative stress include oltipraz and auranofin (Ma, 2013).

TABLE 2

Examples of toxicities associated with drug-induced oxidative stress (from Deavall et al. 2012)

| Therapeutic class | Drug | Example toxicities | Evidence for oxidative stress |
|---|---|---|---|
| Antineoplastic (anthracycline) | Doxorubicin | Cardiac toxicity | Reduction of doxorubicin to free radical increases ROS in cardiomyocytes. Lipid peroxidation, mitochondrial dysfunction, apoptosis |
| Antiretroviral | AZT | Skeletal myopathy, cardiac toxicity | Increased ROS and NOS (peroxide and peroxynitrate). Overexpression of superoxidase dismutase/catalase protects against toxicity, apoptosis |
| Anti-inflammatory | Diclofenac | Nephrotoxicity, hepatotoxicity | Oxidative stress generated by a cation radical or redox cycling of intermediates derived from hydroxylation. Multifactorial perturbations in mitochondrial dysfunction |
| Analgesia | Paracetamol | Hepatotoxicity | Formation of reactive metabolite, depletion of glutathione, activation of proapoptotic proteins. Mitochondrial dysfunction, inflammation |
| Antineoplastic (platinum) | Cisplatin | Nephrotoxicity, ototoxicity | Increases in superoxide anion, hydrogen peroxide, and hydroxyl radical. Depletion of antioxidants GSH-peroxidase and GSH-reductase. Mitochondrial dysfunction, apoptosis |
| Antipsychotic | Chlorpromazine | Dermal toxicity (due to phototoxicity) | Generation of singlet oxygen and superoxide in response to UVA/B irradiation |

In accordance with the present invention, the person skilled in the art is well aware that the presence and degree of oxidative stress may be determined and quantified by suitable biomarker assays known in the art. Respective examples for these markers are given below, but these shall be not construed as limiting possibilities to measure oxidative stress in accordance with the invention:

Markers of Oxidative Stress for Assessment: Serum, Erythrocytes, CSF, Saliva, Urine Free radicals can damage biological molecules including nucleic acids, proteins, and lipids. The products of these reactions can become markers of oxidative stress. Serum is the most common material for the evaluation of the components of oxidative stress. It allows the estimation of most enzymes, substrates, and products of redox reactions. These enzymes include xanthine oxidase, NOS, lipoxygenase, cyclooxygenase, myeloperoxidase, prolyl-oligopeptidase, nicotinamide adenine dinucleotide phosphate-oxidase 1 (NOX1), and NADPH-dependent oxidase. The following are markers of oxidative lipid damage: isoprostanes (IsoP-prostaglandin like substances), for example, 8-iso-prostaglandin (F2α-8-iso-PGF2α) which constitutes the product of lipid peroxidation of arachidonic acid, malondialdehyde (MDA), the formation of fluorescent peroxidized lipid-protein covalent adducts, and the increase in conjugated diene. Oxidative stress involves the oxidation of proteins and glycoxidation. The following are the results of this reaction: the glycophore content, the total level of advanced protein oxidation (AOPP), protein carbonyls, dityrosine level, N'-formylkynurenine, and a decreased level of serum protein thiol groups. Other specific markers of protein oxidation are tyrosine (a marker for hydroxyl radical) and 3-nitrotyrosine (a marker for RNS). Furthermore, 3-nitrotyrosine is a specific marker of peroxynitrite-induced cellular damage. Other indicators in the serum include kynurenine, N'-formylkynurenine, thioredoxin, and 8-hydroxy-2'-deoxyguanosine.

Respective measurements of biomarkers for oxidative stress in humans are summarized in Ilaria Marrocco, Fabio Altieri, and Ilaria Peluso; Review Article: Measurement and Clinical Significance of Biomarkers of Oxidative Stress in Humans; Oxidative Medicine and Cellular Longevity Volume 2017 (2017), Article ID 6501046, 32 pages.

Moreover, in accordance with the present invention, the person skilled in the art is well aware that the bioactivity of DPP3, which is influenced by the herein disclosed DPP3 binder, can be measured for e.g. inhibition via suitable assays known in the art. Respective examples are given below, but these shall be not construed as limiting possibilities to determine DPP3 bioactivity:

Method for Detecting and Measuring the Inhibition of DPP3

Inhibition of DPP3 activity in a liquid phase assay by a binder may be determined as followed: Blood samples (e.g. serum, heparin-plasma, Li-plasma, citrate-plasma, whole blood) of patients before and after anti-DPP3 antibody treatment is incubated with specific DPP3 substrates in a liquid phase assay. The specific liquid phase DPP3 activity assay to determine the inhibitory ability of inhibitory DPP3 antibodies in blood samples comprises the following steps:

Addition of 20 µl blood sample in 200 µl 50 mM Tris-HCl, pH 7.5 in a black non-binding microtiter plate (96-well). Hereby, the person skilled in the art is aware that buffering conditions, concentrations and pH etc. can be varied.

Addition of the fluorogenic substrate Arg-Arg-βNA (20 µl, 2 mM).

Incubation at 37° C. and monitoring the generation of free βNA in a Twinkle LB 970 microplate fluorometer (Berthold Technologies GmbH) over 1 hour. Fluorescence of βNA is detected by exciting at 340 nm and measuring emission at 410 nm.

Slopes (in RFU/min) of increasing fluorescence of the different samples are calculated.

Analysis of DPP3 activity values before and after anti-DPP3 antibody treatment.

In contrast thereto a solid phase assay is an assay where the respective binding events take place at the solid phase. Inhibition of DPP3 activity in a solid phase assay by a binder may be determined as followed according: Blood samples (e.g. serum, plasma, whole blood) of patients before and after anti-DPP3 antibody treatment are contacted with an immobilized capture-binder for enzyme capture activity assay (ECA) on a solid phase. Preferably, as capture-binder for the ECA is chosen the one with the least inhibitory ability. The capture-binder should inhibit DPP3 activity less than 50%, preferably less than 40%, preferably less than 30%. The specific liquid phase DPP3 activity assay to determine the inhibitory ability of possible capture-binders is described in detail in Example 1 below.

The ECA to determine the inhibitory ability of inhibitory DPP3 antibodies in blood samples comprises the following steps:
Contacting said sample with a capture-binder that binds to full-length DPP3 but preferably inhibits DPP3 activity in a liquid phase assay less than 50%, preferably less than 40%, more preferably 30%
Separating DPP3 bound to said capture binder from bodily fluid sample,
Adding substrate of DPP3 to said separated DPP3,
Quantifying DPP3 activity by measuring the conversion of the substrate of DPP3,
Evaluation of measured signals and analysis of DPP3 activity values before and after anti-DPP3 antibody treatment.

The method for determining active DPP3 may be conducted as liquid phase assay and as solid phase assay. Inhibition of DPP3 activity may be determined in a liquid assay nevertheless according to the above-described procedure.

In yet another embodiment, a capture or binding assay may be performed to detect and/or quantitate the protease activity of DPP3. For example, an antibody reactive with DPP3 protein, but which does not interfere with peptidase activity, may be immobilized upon a solid phase. The test sample is passed over the immobile antibody, and DPP3, if present, binds to the antibody and is itself immobilized for detection. A substrate may then be added, and the reaction product may be detected to indicate the presence or amount of DPP3 in the test sample. For the purposes of the present description, the term "solid phase" may used to include any material or vessel in which or on which the assay may be performed and includes, but is not limited to, porous materials, nonporous materials, test tubes, wells, slides, etc.

Moreover, in accordance with the present invention, the person skilled in the art is well aware that the binding affinity of the herein disclosed DPP3 binder to DPP3 may be measured by various suitable assays known in the art. Respective examples are given below, but these shall be not construed as limiting possibilities to measure binding affinity of the herein disclosed DPP3 binder to DPP3:

Method for Measuring the Binding Affinity of the DPP3 Binder of the Invention to the Epitope According to Sequence SEQ ID NO.: 2

The binding affinity of the DPP3 binder to the epitope according to SEQ ID NO.: 2 in accordance with the invention may be determined in accordance with Example 1 and as further set out below:

A binding assay may be performed to detect and/or quantitate antibody binding to the immunization peptide (i.e. SEQ ID NO.: 2). For example, this immunization peptide may be immobilized upon a solid phase. The test sample (e.g. antibody solution) is passed over the immobile immunization peptide, and bound antibody can be detected. For the purposes of the present description, the term "solid phase" may be used to include any material or vessel in which or on which the assay may be performed and includes, but is not limited to, porous materials, nonporous materials, test tubes, wells, slides, etc.

Exemplary detection methods:
Label antibody before contacting with solid phase and detect respective label (fluorescence, chemiluminescence, enzymatic etc.)
Use labeled secondary antibody against specific Fc part of sample-antibody. Incubate solid phase bound antibody with secondary antibody (e.g. anti human IgG, anti murine IgG) and detect respective label (fluorescence, chemiluminescence, enzymatic etc.)
Use a labeled antibody as competitor for solid phase binding (e.g. labeled AK1967).
Quantifiy binding affinity by decrease of signal.

FURTHER DESCRIPTION OF THE INVENTION

Binder Directed Against Circulating, Intracellular, Membranous DPP3

In another embodiment of the invention, the herein disclosed binder of the invention, and DPP3 binder, specifically the anti-DPP3 antibodies, anti-DPP3 antibody fragments, or anti-DPP3 non-Ig scaffolds are capable to bind circulating DPP3, and thus are directed against circulating DPP3.

In yet another embodiment of the invention, the herein disclosed binder of the invention, and DPP3 binder, specifically the anti-DPP3 antibodies, anti-DPP3 antibody fragments, or anti-DPP-3 non-Ig scaffolds are capable to bind intracellular DPP3, and thus are directed against intracellular DPP3.

In yet another embodiment of the invention, the herein disclosed binder of the invention, DPP3 binder, specifically the anti-DPP3 antibodies, anti-DPP3 antibody fragments, or anti-DPP3 non-Ig scaffolds are capable to bind membranous DPP3, and thus are directed against membranous DPP3.

Also subject matter of the present invention, are the herein disclosed binder of the invention, DPP3 binder, specifically is an anti-DPP3 antibody or an anti-DPP3 antibody fragment or an anti-DPP3 non-Ig scaffold for use in the prevention or treatment of diseases or acute conditions in a patient, wherein said diseases or acute conditions are associated with oxidative stress, and whereby said binder, DPP3 binder, specifically is an anti-DPP3 antibody or an anti-DPP3 antibody fragment or an anti-DPP3 non-Ig scaffold are directed to and binding to an epitope of SEQ ID NO.: 2, wherein said epitope is comprised in a circulating DPP3 protein or functional derivative thereof.

Also subject matter of the present invention, are the herein disclosed binder of the invention, DPP3 binder, specifically an anti-DPP3 antibody or an anti-DPP3 antibody fragment or an anti-DPP3 non-Ig scaffold for use in the prevention or treatment of diseases or acute conditions in a patient, wherein said diseases or acute conditions are associated with oxidative stress, and whereby said binder, DPP3 binder, specifically an anti-DPP3 antibody or an anti-DPP3 antibody fragment or an anti-DPP3 non-Ig scaffold are directed to and binding to an epitope of SEQ ID NO.: 2, wherein said epitope is comprised in an intracellular DPP3 protein or functional derivative thereof.

Also subject matter of the present invention, are the herein disclosed binder of the invention, DPP3 binder, specifically an anti-DPP3 antibody or an anti-DPP3 antibody fragment or an anti-DPP3 non-Ig scaffold for use in the prevention or treatment of diseases or acute conditions in a patient, wherein said diseases or acute conditions are associated with oxidative stress, and whereby said DPP3 binder, specifically an anti-DPP3 antibody or an anti-DPP3 antibody fragment or an anti-DPP3 non-Ig scaffold are directed to and binding to an epitope of SEQ ID NO.: 2, wherein said epitope is comprised in a membranous DPP3 protein or functional derivative thereof.

Subject matter of the present invention is further a method for regulating and/or preventing or treatment of oxidative stress in a patient having a chronic or acute disease or acute condition, characterized in that to said patient a binder of the invention, or a DPP3 binder of the invention, specifically an anti-DPP3 antibody or an anti-DPP3 antibody fragment or an anti-DPP3 non-Ig scaffold is administered in pharmaceutically effective amounts. According to the invention said patient is a patient in need of regulating and/or preventing or in need of treatment of oxidative stress.

Pharmaceutical Composition

Another subject of the present invention is a pharmaceutical composition comprising the herein disclosed binder of the invention, or DPP3 binder, specifically comprising an anti-DPP3 antibody or an anti-DPP3 antibody fragment or an anti-DPP3 non-Ig scaffold for use in the prevention or treatment of diseases or acute conditions of a patient, wherein said disease or acute condition is associated with oxidative stress.

In another embodiment of the present invention said pharmaceutical composition is a solution, preferably a ready-to-use solution.

In another embodiment of the present invention said pharmaceutical composition is a solution, preferably a ready-to-use solution comprising PBS at a pH of 7.4.

In another embodiment of the present invention said pharmaceutical composition is in a dried state that is to be reconstituted before use.

In another embodiment of the present invention said pharmaceutical composition is in a freeze-dried state that is to be reconstituted before use.

Administration Routes

In another embodiment of the present invention said pharmaceutical composition that is to be used in the prevention and/or treatment of a disease or an acute condition of a patient, wherein said disease or acute condition is associated with oxidative stress is administered orally, epicutaneously, subcutaneously, intradermally, sublingually, intramuscularly, intraarterially, intracerebrally, intracerebroventricularly, intravenously, or via the central nervous system (CNS) or via intraperitoneal administration.

Kit

Another embodiment of the present invention is a kit or an assay comprising the herein disclosed binder of the invention, or DPP3 binder, specifically comprising an anti-DPP3 antibody or an anti-DPP3 antibody fragment or an anti-DPP3 non-Ig scaffold for use in the prevention or treatment of a disease or acute condition of a patient, whereby said disease or acute condition is associated with oxidative stress.

Specifically Binding Antibodies

In accordance with the invention the "anti-DPP3 antibody" is an antibody that binds specifically to DPP3, an "anti-DPP3 antibody fragment" is a fragment of said anti-DPP3 antibody, wherein said fragment binds specifically to DPP3. An "anti-DPP3 non-Ig scaffold" is a non-Ig scaffold that binds specifically to DPP3.

With the context of the invention, "specifically binding to DPP3" may also allow binding to other antigens as well. This means, this specificity would not exclude that the binder may cross-react with other proteins or polypeptides or peptides that contain the epitope according to SEQ ID NO.: 2 against which the binder has been raised. This specifically includes functional variants of DPP3, which also comprise an epitope according to SEQ ID NO.: 2. This also pertains to the specificity of the anti-DPP3 antibody fragment or anti-DPP3 non-Ig scaffold in accordance with the invention.

Antibody

An "antibody" according to the present invention is a protein including one or more polypeptides substantially encoded by immunoglobulin genes that specifically binds an antigen. The recognized immunoglobulin genes include the kappa, lambda, alpha (IgA), gamma (IgG$_1$, IgG$_2$, IgG$_3$, IgG$_4$), delta (IgD), epsilon (IgE) and mu (IgM) constant region genes, as well as the myriad immunoglobulin variable region genes. Full-length immunoglobulin light chains are generally about 25 kDa or 214 amino acids in length.

Full-length immunoglobulin heavy chains are generally about 50 kDa or 446 amino acids in length. Light chains are encoded by a variable region gene at the NH$_2$-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and F(ab')$_2$, as well as bifunctional hybrid antibodies and single chains (e.g., Lanzavecchia et al., *Eur. J. Immunol.* 17:105, 1987; Huston et al., *Proc. Natl. Acad. Sci. U.S.A.*, 85:5879-5883, 1988; Bird et al., *Science* 242:423-426, 1988; Hood et al., *Immunology*, Benjamin, N.Y., 2nd ed., 1984; Hunkapiller and Hood, *Nature* 323:15-16, 1986).

An immunoglobulin light or heavy chain variable region includes a framework region interrupted by three hypervariable regions, also called complementarity determining regions (CDR's) (see, *Sequences of Proteins of Immunological Interest*, E. Kabat et al., U.S. Department of Health and Human Services, 1983). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

"Chimeric antibodies" are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No.

5,807,715. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor."

In one embodiment of the invention, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences.

A "humanized antibody" in accordance with the invention is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO 91/17271; McCafferty et al., PCT Publication No. WO 92/001047; and Winter, PCT Publication No. WO 92/20791), or selected from a human combinatorial monoclonal antibody library (see the Morphosys website). Human antibodies can also be prepared by using transgenic animals carrying a human immunoglobulin gene (for example, see Lonberg et al., PCT Publication No. WO 93/12227; and Kucherlapati, PCT Publication No. WO 91/10741).

Thus, the anti-DPP3 antibody or anti-DPP3 antibody fragment in accordance with the invention may have the formats known in the art. Examples are human antibodies, monoclonal antibodies, humanized antibodies, chimeric antibodies, CDR-grafted antibodies or antibody fragments thereof, but not limited to.

Monoclonal Antibody

In a specific embodiment of the invention the anti-DPP3 antibody is a monoclonal antibody or a fragment thereof. In one embodiment of the invention the anti-DPP3 antibody or the anti-DPP3 antibody fragment is a human or humanized antibody or derived therefrom. In one specific embodiment one or more (murine) CDR's are grafted into a human antibody or antibody fragment.

In a preferred embodiment antibodies according to the present invention are recombinantly produced antibodies as e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')$_2$-fragments, scFv-fragments, multimerized multivalent and/or multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines and numerous others.

Non-Ig Scaffolds

In addition to anti-DPP3 antibodies or anti-DPP3 antibody fragments, other biopolymer scaffolds, so called non-Ig scaffolds, are well known in the art to complex a target molecule and have been used for the generation of highly target specific biopolymers. Examples are aptamers, spiegelmers, anticalins and conotoxins.

Non-Ig scaffolds with the context of the invention may be protein scaffolds and may be used as antibody mimics as they are capable to bind to ligands or antigens. Non-Ig scaffolds may be selected from the group comprising tetranectin-based non-Ig scaffolds (e.g. described in US 2010/0028995), fibronectin scaffolds (e.g. described in EP 1266 025; lipocalin-based scaffolds (e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microprotein (preferably microproteins forming a cystine knot) scaffolds (e.g. described in EP 2314308), Fyn SH3 domain based scaffolds (e.g. described in WO 2011/023685), EGFR-A-domain based scaffolds (e.g. described in WO 2005/040229) and Kunitz domain based scaffolds (e.g. described in EP 1941867). Non-Ig scaffolds may be peptide or oligonucleotide aptamers. Aptamers are usually created by selecting them from a large random sequence pool and are either short strands of oligonucleotides (DNA, RNA or XNA; Xu et al. 2010, Deng et al. 2014) or short variable peptide domains attached to a protein scaffold (Li et al. 2011).

Fragments and Fusion Proteins

In an alternative embodiment the anti-DPP3 antibody format is selected from the group comprising Fv fragment, scFv fragment, Fab fragment, scFab fragment, F(ab)$_2$ fragment and scFv-Fc Fusion protein. In another preferred embodiment the antibody format is selected from the group comprising scFab fragment, Fab fragment, scFv fragment and bioavailability optimized conjugates thereof, such as PEGylated fragments.

Monoclonal/Polyclonal Antibodies

With the context of the invention, the term "antibody" generally comprises monoclonal and polyclonal antibodies and binding fragments thereof, in particular Fc-fragments as well as so called "single-chain-antibodies" (Bird et al. 1988), chimeric, humanized, in particular CDR-grafted antibodies, and di- or tetrabodies (Holliger et al. 1993). Also comprised are immunoglobulin-like proteins that are selected through techniques including, for example, phage display to specifically bind to the molecule of interest contained in a sample. In this context the term "specific binding" refers to antibodies raised against the molecule of interest or a fragment thereof. An antibody is considered to be specific, if its affinity towards the molecule of interest or the aforementioned fragment thereof is at least preferably 50-fold higher, more preferably 100-fold higher, most preferably at least 1000-fold higher than towards other molecules comprised in a sample containing the molecule of interest. It is well known in the art how to make antibodies and to select antibodies with a given specificity.

In a specific embodiment of the invention said anti-DPP3 antibody or anti-DPP3 antibody fragment binding to an epitope according to SEQ ID NO.: 2, wherein said epitope is comprised in a DPP3 protein or functional derivative thereof is a monoclonal antibody or a monoclonal antibody fragment thereof. In one embodiment of the invention the anti-DPP3 antibody or the anti-DPP3 antibody fragment binding to an epitope according to SEQ ID NO.: 2, wherein said epitope is comprised in a DPP3 protein or functional derivative thereof is a human or humanized antibody or derived therefrom or humanized antibody fragment or derived therefrom.

In one specific embodiment one or more (murine) CDR's are grafted into a human antibody or antibody fragment.

A Modulating Anti-DPP3 Antibody

In a specific embodiment said DPP3 binder of the invention, specifically said anti-DPP3 antibody, anti-DPP3 antibody fragment or anti-DPP3 non-Ig scaffold is a modulating DPP3 binder, anti-DPP3 antibody, anti-DPP3 antibody fragment or anti-DPP3 non-Ig scaffold.

A modulating DPP3 binder, anti-DPP3 antibody, anti-DPP3 antibody fragment or anti-DPP3 non-Ig scaffold of the invention may act inhibitory and may block the bioactivity of DPP3 to nearly 100%, preferably to at least more than 90%, more preferably to at least 80, or 70, or 60, or 50, or 40, or 30, or 20, or 10% when determined by means of the above described method for detecting and measuring the inhibition of DPP3; i.e. measuring the DPP3 binder influence on DPP-3 bioactivity.

In another specific embodiment, a modulating DPP3 binder, anti-DPP3 antibody, anti-DPP3 antibody fragment or anti-DPP3 non-Ig scaffold of the invention may act upregulating and thus may enhance the bioactivity of DPP3 to at least 50%, preferably to at least more than 60%, more preferably to at least more than 70%, more preferably to at least more than 80%, even more preferably to at least more than 90%, even more so preferably to at least 95% when determined by means of the above described method for detecting and measuring the inhibition of DPP3; i.e. measuring the DPP3 binder influence on DPP-3 bioactivity.

Synthesis of Anti-DPP3 Antibodies

Anti-DPP3 antibodies according to the present invention may be synthesised as follows:

DPP3 peptides for immunization were synthesized, see table 3 below, (JPT Technologies, Berlin, Germany) with an additional N-terminal cystein (if no cystein is present within the selected DPP3-sequence) residue for conjugation of the peptides to Bovine Serum Albumin (BSA). The peptides were covalently linked to BSA by using Sulfolink-coupling gel (Perbio-science, Bonn, Germany) The coupling procedure was performed according to the manual of Perbio. Recombinant GST-hDPP3 was produced by USBio.

Balb/c mice were intraperitoneally (i.p.) injected with 84 µg GST-hDPP3 or 100 µg DPP3-peptide-BSA-conjugates at day 0 (emulsified in TiterMax Gold Adjuvant), 84 µg or 100 µg at day 14 (emulsified in complete Freund's adjuvant) and 42 µg or 50 µg at day 21 and 28 (in incomplete Freund's adjuvant). At day 49 the animal received an intravenous (i.v.) injection of 42 µg GST-hDPP3 or 50 µg DPP3-peptide-BSA-conjugates dissolved in saline. Three days later the mice were sacrificed and the immune cell fusion was performed.

Splenocytes from the immunized mice and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After one week, the HAT medium was replaced with HT Medium for three passages followed by returning to the normal cell culture medium.

The cell culture supernatants were primarily screened for recombinant DPP3 binding IgG antibodies two weeks after fusion. Therefore, recombinant GST-tagged DPP3 (USBiologicals, Salem, USA) was immobilized in 96-well plates (100 ng/well) and incubated with 50 µl cell culture supernatant per well for 2 hours at room temperature. After washing of the plate, 50 µl/well POD-rabbit anti mouse IgG was added and incubated for 1 h at RT.

After a next washing step, 50 µl of a chromogen solution (3.7 mM o-phenylendiamin in citrate/hydrogen phosphate buffer, 0.012% $H_2O_2$) were added to each well, incubated for 15 minutes at RT and the chromogenic reaction stopped by the addition of 50 µl 4N sulfuric acid. Absorption was detected at 490 mm The positive tested microcultures were transferred into 24-well plates for propagation. After retesting the selected cultures were cloned and recloned using the limiting-dilution technique and the isotypes were determined.

Antibodies raised against GST-tagged human DPP3 or DPP3-peptides were produced via standard antibody production methods (Marx et al. 1997) and purified via Protein A. The antibody purities were >90% based on SDS gel electrophoresis analysis.

Humanization of Murine Antibodies

Humanization of murine antibodies may be conducted according to the following procedure:

For humanization of an antibody of murine origin the antibody sequence is analyzed for the structural interaction of framework regions (FR) with the complementary determining regions (CDR) and the antigen. Based on structural modelling an appropriate FR of human origin is selected and the murine CDR sequences are transplanted into the human FR. Variations in the amino acid sequence of the CDRs or FRs may be introduced to regain structural interactions, which were abolished by the species switch for the FR sequences. This recovery of structural interactions may be achieved by random approach using phage display libraries or via directed approach guided by molecular modeling (Almagro J C, Fransson J., 2008. Humanization of antibodies. Front Biosci. 2008 Jan. 1; 13:1619-33).

CDR-Grafted Antibodies

In another aspect of the invention, the provided subject matter is a human CDR-grafted anti-DPP3 antibody or anti-DPP3 antibody fragment thereof that is directed to and binding to an epitope according to SEQ ID NO.: 2, wherein said epitope is comprised in a DPP3 protein or a functional derivative thereof, and wherein said human CDR-grafted anti-DPP3 antibody or anti-DPP3 antibody fragment thereof comprises an antibody heavy chain variable region (H chain) comprising SEQ ID NO.: 5
and/or further comprises an antibody light chain variable region (L chain) comprising:

SEQ ID NO.: 6.

Further subject matter of the present invention in another aspect is a human CDR-grafted anti-DPP3 antibody or anti-DPP3 antibody fragment thereof that is directed to and binding to an epitope according to SEQ ID NO.: 2, wherein said epitope is comprised in a DPP3 protein or a functional derivative thereof, and wherein the said human CDR-grafted anti-DPP3 antibody or anti-DPP3 antibody fragment thereof comprises an antibody heavy chain variable region (H chain) comprising:

SEQ ID NO.: 12 and/or further comprises an antibody light chain variable region (L chain) comprising:

SEQ ID NO.: 13.

In one specific embodiment of the invention subject matter of the present invention is a human monoclonal anti-DPP3 antibody or monoclonal anti-DPP3 antibody fragment thereof that is directed to and binding to an epitope according to SEQ ID NO.: 2, wherein said epitope is comprised in a DPP3 protein or a functional derivative thereof, and wherein the heavy chain comprises at least one CDR of:

SEQ ID NO.: 7, SEQ ID NO.: 8 or SEQ ID NO.: 9 and wherein the light chain comprises at least one CDR of:

SEQ ID NO.: 8, KVS or SEQ ID NO.: 11.

With the above context, the variable region can be connected to any subclass of constant regions (IgG, IgM, IgE. IgA), or only scaffolds, Fab fragments, Fv, Fab and F(ab)2. In example 3 below, the murine antibody variant with an IgG2a backbone was used. For chimerization and humanization a human IgG1κ backbone was used.

Epitope Binding

For epitope binding only the Complementarity Determining Regions (CDRs) are of importance. The CDRs for the heavy chain and the light chain of the murine anti-DPP3 antibody of the present invention (AK1967) are shown in SEQ ID NO. 7, SEQ ID NO. 8 and SEQ ID NO. 9 for the heavy chain and SEQ ID NO. 10, sequence KVS and SEQ ID NO. 11 for the light chain, respectively.

Epitope Binding Sites

In accordance with the invention, the herein provided DPP3 binder, specifically the herein provided anti-DPP3 antibodies, anti-DPP3 antibody fragments and anti-DPP3 non Ig-scaffolds are directed to and binding to SEQ ID NO.: 1, and wherein said DPP3 binder, anti-DPP3 antibody, anti-DPP3 antibody fragment and anti-DPP3 non Ig-scaffold recognizes and binds to at least three aa, preferably at least 4 aa, more preferably at least 5 aa, even more preferably at least 6 aa of said SEQ ID NO.:1.

In accordance with the invention, the herein provided DPP3 binder, specifically the herein provided anti-DPP3 antibodies, anti-DPP3 antibody fragments and anti-DPP3 non Ig-scaffolds are directed to and binding to an epitope according to SEQ ID NO.: 2, wherein said epitope is comprised in a DPP3 protein or a functional derivative thereof, and wherein said DPP3 binder, anti-DPP3 antibody, anti-DPP3 antibody fragment and anti-DPP3 non Ig-scaffold recognizes and binds to at least three aa, preferably at least 4 aa, more preferably at least 5 aa, even more preferably at least 6 aa of SEQ ID NO.: 2.

In another aspect of the invention, the herein provided DPP3 binder, specifically the herein provided anti-DPP3 antibodies, anti-DPP3 antibody fragments and anti-DPP3 non Ig-scaffolds are directed to and binding to an epitope according to SEQ ID NO.: 3, and wherein said epitope according to SEQ ID NO.: 3 is comprised in a DPP3 protein or a functional derivative thereof, and wherein said DPP3 binder, anti-DPP3 antibody, anti-DPP3 antibody fragment and anti-DPP3 non Ig-scaffold recognizes and binds to at least three aa, preferably at least 4 aa, more preferably at least 5 aa, even more preferably to 6 aa of SEQ ID NO.: 3.

In another aspect of the invention, the herein provided DPP3 binder, specifically the herein provided anti-DPP3 antibodies, anti-DPP3 antibody fragments and anti-DPP3 non Ig-scaffolds are directed to and binding to an epitope according to SEQ ID NO.: 4, and wherein said epitope according to SEQ ID NO.: 4 is comprised in a DPP3 protein or a functional derivative thereof, and wherein said DPP3 binder, anti-DPP3 antibody, anti-DPP3 antibody fragment and anti-DPP3 non Ig-scaffold recognizes and binds to at least three aa, preferably to four aa of SEQ ID NO.: 4.

Inhibitor or Effector of the Bioactivity of DPP3

In a specific embodiment of the invention, the herein provided DPP3 binder, specifically the herein provided anti-DPP3 antibodies, anti-DPP3 antibody fragments and anti-DPP3 non Ig-scaffolds which are directed to and binding to an epitope according to SEQ ID NO.: 2, wherein said epitope is comprised in a DPP3 protein or a functional derivative thereof, may act as inhibitor or effector of the bioactivity of DPP3.

Thus, the herein provided DPP3 binder, specifically the herein provided anti-DPP3 antibodies, anti-DPP3 antibody fragments and anti-DPP3 non Ig-scaffolds which are directed to and binding to an epitope according to SEQ ID NO.: 2, wherein said epitope is comprised in a DPP3 protein or a functional derivative thereof are useful in the prevention or treatment of a disease or acute condition in a patient, wherein said disease or acute condition is associated with oxidative stress in accordance with the invention.

Affinity

In a specific embodiment of the invention, the herein provided DPP3 binder, specifically the herein provided anti-DPP3 antibodies, anti-DPP3 antibody fragments and anti-DPP3 non Ig-scaffolds which are directed to and binding to an epitope according to SEQ ID NO.: 2, wherein said epitope is comprised in a DPP3 protein or a functional derivative thereof, exhibit an affinity towards DPP3 in such that the affinity constant is at least $10^{-7}$ M$^{-1}$, preferably at least $10^{-8}$ M$^{-1}$, more preferably the affinity constant is at least $10^{-9}$ M$^{-1}$, most preferred the affinity constant is at least $10^{-10}$ M$^{-1}$ when determined by means of the methods for measuring the binding affinity of the DPP3 binder of the invention to the epitope according to sequence SEQ ID NO.: 2 as described above.

Thereby, a person skilled in the art knows that it may be considered to compensate lower affinity by applying a higher dose of binder; e.g. an anti-DPP3 antibody or anti-DPP3 antibody fragment or anti-DPP3 non-Ig scaffold, and this measure would not lead out-of-the-scope of the invention.

Drug Combinations

In another embodiment of the invention, the herein provided DPP3 binder, specifically the herein provided anti-DPP3 antibody or anti-DPP3 antibody fragment thereof or anti-DPP3 non-Ig scaffold may be used in combination with at least one additional drug that induces oxidative stress as side effect.

Such drugs are administered as primary medicament for use in the prevention or treatment of a primary disease and may be selected from a group comprising antimicrobials like antibiotics (for example streptomycin, gentamicin) or antivirals (for example acyclovir, foscarnet) or antifungal (for example amphotecerin B), analgesics, non-steroidal anti-inflammatory drugs (NSAID) (for example ibuprofen, naproxen), diuretics, proton pump inhibitors, chemotherapeutics (for example cisplatin), contrast dyes, cardiovascular agents like ACE-inhibitors or statins, anti-depressants, immune suppressants (for example cyclosporine A) and antihistamines Thereby, and in accordance with the invention, the herein provided DPP3 binder, specifically the herein provided anti-DPP3 antibody or anti-DPP3 antibody fragment thereof or a DPP3 non-Ig scaffold binding to DPP3 may be used as secondary medicament either in combination or as stand-alone drug in the prevention or treatment of the induced oxidative stress and resultant toxicities as secondary diseases.

Selective/Specific Binder

In a preferred embodiment of the invention the herein provided DPP3 binder are pharmaceutically acceptable, selective and/or specific for an epitope according to SEQ ID NO.: 2, which is comprised in a DPP3 protein or a functional derivative thereof.

In a more preferred embodiment of the invention the herein provided DPP3 binder is an inhibitory binder that is pharmaceutically acceptable, selective and/or specific for an epitope according to SEQ ID NO.: 2, which is comprised in a DPP3 protein or a functional derivative thereof.

In one aspect of the invention, selective and specific inhibitors of DPP3 do not bind to other proteins/peptides/enzymes or are bound by other proteins/peptides/enzymes, and do not inhibit any other enzyme/protease/peptidase other than DPP3. Therefore, the preferred inhibitors of DPP3 bioactivity with the context of the invention are specific anti-DPP3 antibodies, antibody fragments or non-Ig scaffolds binding to DPP3.

Monospecific Antibody

Monospecific anti-DPP3 antibody or monospecific anti-DPP3 antibody fragment or monospecific anti-DPP3 non-Ig scaffold with the context of the invention means that said antibody or antibody fragment or non-Ig scaffold binds specifically to one specific region encompassing at least 3 amino acids, preferably at least 4 aa within the target DPP3.

With the context of the invention, monospecific anti-DPP3 antibody or monospecific anti-DPP3 antibody fragment or monospecific anti-DPP3 non-Ig scaffold are anti-DPP3 antibodies or anti-DPP3 antibody fragments or anti-DPP3 non-Ig scaffolds all have affinity for the same antigen as a target which is in accordance with the invention an epitope according to SEQ ID NO.: 2, which is comprised in a DPP3 protein or a functional derivative thereof.

In another specific embodiment, monospecific anti-DPP3 antibody or monospecific anti-DPP3 antibody fragment or monospecific anti-DPP3 non-Ig scaffold are anti-DPP3 antibodies or anti-DPP3 antibody fragments or anti-DPP3 non-Ig scaffolds all have affinity for the same antigen as a target which is in accordance with the invention an epitope according to SEQ ID NO.: 3, which is comprised in a DPP3 protein or a functional derivative thereof.

In another embodiment, monospecific anti-DPP3 antibody or monospecific anti-DPP3 antibody fragment or monospecific anti-DPP3 non-Ig scaffold are anti-DPP3 antibodies or anti-DPP3 antibody fragments or anti-DPP3 non-Ig scaffolds all have affinity for the same antigen as a target which is in accordance with the invention an epitope according to SEQ ID NO.: 4, which is comprised in a DPP3 protein or a functional derivative thereof.

Monospecific antibodies may also be produced by other means than producing them from a common germ cell.

With the above context, further preferred embodiments within the scope of the present invention are consecutively numbered below:

1. A binder directed to and binding to an epitope according to SEQ ID NO.: 2, and wherein said binder recognizes and binds to at least three amino acids of SEQ ID NO.: 2, and wherein said epitope is comprised in SEQ ID NO.: 1, which corresponds to the amino acid sequence of DPP3.

2. The binder directed to and binding to an epitope according to SEQ ID NO.: 2 of embodiment 1, wherein said binder is directed to and binding to an epitope according to SEQ ID NO.: 3, and wherein said binder recognizes and binds to at least three amino acids of SEQ ID NO.: 3, and wherein said epitope is comprised in SEQ ID NO.: 1, which corresponds to the amino acid sequence of DPP3.

3. The binder directed to and binding to an epitope according to SEQ ID NO.: 2 of embodiment 1 or embodiment 2, wherein said binder is directed to and binding to an epitope according to SEQ ID NO.: 4, and wherein said binder recognizes and binds to at least three amino acids of SEQ ID NO.: 4, and wherein said epitope is comprised in SEQ ID NO.: 1, which corresponds to the amino acid sequence of DPP3.

4. The binder directed to and binding to an epitope according to SEQ ID NO.: 2 of any of the embodiments 1 to 3, wherein said binder is selected from a group comprising an antibody or antibody fragment or non-Ig scaffold, and wherein said epitope is comprised in SEQ ID NO.: 1, which corresponds to the amino acid sequence of DPP3.

5. The binder directed to and binding to an epitope according to SEQ ID NO.: 2 of any of the preceding embodiments, wherein said binder is a dipeptidyl peptidase 3 (DPP3) binder directed to and binding to an epitope according to SEQ ID NO.: 2, wherein said epitope is comprised in a DPP3 protein or a functional derivative thereof, and wherein said DPP3 binder recognizes and binds to at least three amino acids of SEQ ID NO.: 2.

6. The binder directed to and binding to an epitope according to SEQ ID NO.: 2 of any of the preceding embodiments, wherein said binder is a monoclonal antibody or monoclonal antibody fragment, and wherein the complementarity determining regions (CDR's) in the heavy chain comprises the sequences:
SEQ ID NO.: 7, SEQ ID NO.: 8 and/or SEQ ID NO.: 9
and the complementarity determining regions in the light chain comprises the sequences:
SEQ ID NO.: 10, KVS and/or SEQ ID NO.: 11.

7. The binder directed to and binding to an epitope according to SEQ ID NO.: 2 of any of the preceding embodiments, wherein said binder is a human monoclonal antibody or human monoclonal antibody fragment, wherein the heavy chain comprises the sequence:
SEQ ID NO.: 12
and wherein the light chain comprises the sequence:
SEQ ID NO.: 13.

8. The binder directed to and binding to an epitope according to SEQ ID NO.: 2 of any of the preceding embodiments for use in the prevention or treatment of diseases or acute conditions in a patient, wherein said disease or acute condition is associated with oxidative stress.

9. The binder directed to and binding to an epitope according to SEQ ID NO.: 2 for use in the prevention or treatment of diseases or acute conditions in a patient, wherein said disease or acute condition is associated with oxidative stress according to embodiment 8, wherein said diseases are selected from a group comprising neurodegenerative diseases, metabolic syndrome, cardiovascular disorders, autoimmune diseases, inflammatory lung diseases, kidney diseases, liver diseases, digestive diseases, viral infectious diseases, cancer, inflammation, sepsis, septic shock and SIRS.

10. The binder directed to and binding to an epitope according to SEQ ID NO.: 2 for use in the prevention or treatment of diseases or acute conditions in a patient, wherein said disease or acute condition is associated with oxidative stress according to embodiment 8 or 9, and wherein said:
neurodegenerative disease may be selected from a group comprising Alzheimer's disease (AD), Parkinson's disease (PD), Huntington's disease (HD), amyotrophic lateral sclerosis (ALS) and multiple sclerosis (MS)),
metabolic syndrome may be selected from a group comprising insulin resistance, obesity, hyperglycemia, dyslipidemia, hypertension and diabetes,
cardiovascular disorder may be selected from a group comprising aterosclerosis, hypertension, heart failure, cardiovascular ischemia, cerebral ischemic injury, stroke and myocardial infarction,
autoimmune disease may be selected from a group comprising rheumatoid arthritis, systemic lupus erythematosus,
inflammatory lung disease may be selected from a group comprising COPD, asthma,
kidney disease may be selected from a group comprising acute kidney injury (AKI), chronic kidney disease (CKD), diabetic nephropathy, end-stage renal disease (ESRD),
liver disease may be selected from a group comprising viral hepatitis, and cirrhosis,
digestive disease may be selected from a group comprising inflammatory bowel disease e.g. Ulcerative colitis, Crohn's disease, gastritis, pancreatitis and peptic ulcer,
viral infectious disease may be selected from a group comprising blood-borne hepatitis viruses (B, C, and D), human immunodeficiency virus (HIV), influenza A, Epstein-Barr virus, respiratory syncytial virus,
cancer may be selected from a group comprising prostate cancer, breast cancer, lung cancer, colorectal cancer, bladder cancer, ovarian cancer, skin cancer, stomach cancer, liver cancer,
inflammation,
sepsis, septic shock, SIRS.

11. The binder directed to and binding to an epitope according to SEQ ID NO.: 2 for use in the prevention or treatment of diseases or acute conditions in a patient, wherein said disease or acute condition is associated with oxidative stress according to any of the embodiments 8 to 10, wherein said disease is selected from a group comprising sepsis, septic shock, and SIRS.

12. The binder directed to and binding to an epitope according to SEQ ID NO.: 2 for use in the prevention or treatment of diseases or acute conditions in a patient, wherein said disease or acute condition is associated with oxidative stress according to embodiment 8, wherein said acute condition is selected from a group comprising renal toxicity and hepatotoxicity.

13. The binder directed to and binding to an epitope according to SEQ ID NO.: 2 for use in the prevention or treatment of diseases or acute conditions in a patient, wherein said disease or acute condition is associated with oxidative stress according to any of the embodiments 8 to 12, wherein the binder is an anti-DPP3 antibody or anti-DPP3 antibody fragment or anti-DPP3 non-Ig scaffold binding to an epitope according to SEQ ID NO.: 2, and wherein said epitope is comprised in a DPP3 protein or a functional derivative thereof, and wherein said anti-DPP3 antibody or anti-DPP3 antibody fragment or anti-DPP3 non-Ig scaffold exhibits a binding affinity to DPP3 of at least $10^{-7}$ M.

14. The binder directed to and binding to an epitope according to SEQ ID NO.: 2 for use in the prevention or treatment of diseases or acute conditions in a patient, wherein said disease or acute condition is associated with oxidative stress according to any of the embodiments 8 and 12, wherein said acute condition is hepatotoxicity which is drug-induced or alcohol-induced hepatotoxicity.

15. The binder directed to and binding to an epitope according to SEQ ID NO.: 2 for use in the prevention or treatment of diseases or acute conditions in a patient, wherein said disease or acute condition is associated with oxidative stress according to embodiment 8, wherein said acute condition is renal toxicity which is drug-induced renal toxicity.

16. The binder directed to and binding to an epitope according to SEQ ID NO.: 2 for use in the prevention or treatment of diseases or acute conditions in a patient, wherein said disease or acute condition is associated with oxidative stress according to any of the embodiments 8 to 11, wherein said disease is associated with oxidative stress in the myocard.

17. Pharmaceutical composition comprising a binder according to any of the embodiments 1 to 7 for use in the prevention or treatment of a disease or acute condition of a patient, whereby said disease or acute condition is associated with oxidative stress.

18. A kit comprising a binder according to any of the embodiments 1 to 16.

19. A binder directed to and binding to a DPP3 protein or functional derivative thereof for use in the prevention or treatment of diseases or acute conditions in a patient, wherein said disease or acute condition is associated with oxidative stress.

20. The binder for use in the prevention or treatment of diseases or acute conditions in a patient, wherein said disease or acute condition is associated with oxidative stress according to embodiment 19, wherein said diseases are selected from a group comprising neurodegenerative diseases, metabolic syndrome, cardiovascular disorders, autoimmune diseases, inflammatory lung diseases, kidney diseases, liver diseases, digestive diseases, viral infectious diseases, cancer, inflammation, sepsis, septic shock and SIRS.

21. The binder for use in the prevention or treatment of diseases or acute conditions in a patient, wherein said disease or acute condition is associated with oxidative stress according to any of the embodiments 19 or 20, and wherein said:
neurodegenerative disease may be selected from a group comprising Alzheimer's disease (AD), Parkinson's disease (PD), Huntington's disease (HD), amyotrophic lateral sclerosis (ALS) and multiple sclerosis (MS)), metabolic syndrome may be selected from a group comprising insulin resistance, obesity, hyperglycemia, dyslipidemia, hypertension and diabetes, cardiovascular disorder may be selected from a group comprising aterosclerosis, hypertension, heart failure, cardiovascular ischemia, cerebral ischemic injury, stroke and myocardial infarction, autoimmune disease may be selected from a group comprising rheumatoid arthritis, systemic lupus erythematosus, inflammatory lung disease may be selected from a group comprising COPD, asthma, kidney disease may be selected from a group comprising acute kidney injury (AKI), chronic kidney disease (CKD), diabetic nephropathy, end-stage renal disease (ESRD), liver disease may be selected from a group comprising viral hepatitis, and cirrhosis, digestive disease may be selected from a group comprising inflammatory bowel disease e.g. Ulcerative colitis, Crohn's disease, gastritis, pancreatitis and peptic ulcer, viral infectious disease may be selected from a group comprising blood-borne hepatitis viruses (B, C, and D), human immunodeficiency virus (HIV), influenza A, Epstein-Barr virus, respiratory syncytial virus, cancer may be selected from a group comprising prostate cancer, breast cancer, lung cancer, colorectal cancer, bladder cancer, ovarian cancer, skin cancer, stomach cancer, liver cancer, inflammation, sepsis, septic shock, SIRS.

22. A binder according to any of the embodiments 19 to 21, wherein said binder is directed to and binding to an epitope according to SEQ ID NO.: 2, and wherein said binder recognizes and binds to at least three amino acids of SEQ ID NO.: 2.

23. The binder according any of the embodiments 19 to 22, wherein said binder is directed to and binding to an epitope according to SEQ ID NO.: 3, and wherein said binder recognizes and binds to at least three amino acids of SEQ ID NO.: 3.

24. The binder according to any of the embodiments 19 to 23, wherein said binder is directed to and binding to an epitope according to SEQ ID NO.: 4, and wherein said DPP3 binder recognizes and binds to at least three amino acids of SEQ ID NO.: 4.

25. The binder according to any of the embodiments 19 to 24, wherein said binder is selected from a group comprising an antibody or antibody fragment or non-Ig scaffold.

26. The binder according to any of the embodiments 19 to 25, wherein said binder is a monoclonal antibody or monoclonal antibody fragment, and wherein the complementarity determining regions (CDR's) in the heavy chain comprises the sequences:
SEQ ID NO.: 7, SEQ ID NO.: 8 and/or SEQ ID NO.: 9 and the complementarity determining regions in the light chain comprises the sequences:
SEQ ID NO.: 10, KVS and/or SEQ ID NO.: 11.

27. The binder according any of the embodiments 19 to 26, wherein said binder is a humanized monoclonal antibody or humanized monoclonal antibody fragment, wherein the heavy chain comprises the sequence:
SEQ ID NO.: 12
and wherein the light chain comprises the sequence:
SEQ ID NO.: 13.

28. The binder according to any of the embodiments 19 to 27, wherein said binder is a dipeptidyl peptidase 3 (DPP3) binder directed to and binding to an epitope according to SEQ ID NO.: 2, wherein said epitope is comprised in a DPP3 protein or a functional derivative thereof, and wherein said DPP3 binder recognizes and binds to at least three amino acids of SEQ ID NO.: 2.

Definitions

In accordance with the invention, an "DPP3 binder" is directed to and binding to an epitope according to SEQ ID NO.: 2, wherein said epitope is comprised in a DPP3 protein or a functional derivative thereof, and wherein said DPP3 binder recognizes and binds to at least three aa of SEQ ID NO.: 2 or a respective subsequence thereof according to the SEQ ID NO'S.: 3 or 4.

In accordance with the invention, a DPP3 binder is preferably an anti-DPP3 antibody, or an anti-DPP3 antibody fragment, or an anti-DPP3 non-Ig scaffold directed to and binding to an epitope according to SEQ ID NO.: 2, wherein said epitope is comprised in a DPP3 protein or a functional derivative thereof, and wherein said DPP3 binder recognizes and binds to at least three aa of SEQ ID NO.: 2 or a respective subsequence thereof according to the SEQ ID NO'S.: 3 or 4.

With the context of the invention, a "functional derivative" of a DPP3 protein denotes a peptide, polypeptide or protein that differs from the sequence of SEQ ID NO.: 1 by means of deletion of aa, addition of aa or changes of specific aa, but remains the bioactivity and function of a native DPP3 protein. Thereby, due to the modifications of the SEQ ID NO.: 1 the bioactivity and function may be influenced to a certain extent, but the enzymatic protease reaction catalysed by DDP3 is still maintained when assay by a suitable bioactivity assay as described above or commonly known by the skilled person.

A person skilled in the art understands that a dipeptidyl peptidase 3 (DPP3) antibody or an anti-DPP3 antibody fragment or anti-DPP3 non-Ig scaffold is synonymous to dipeptidyl peptidase 3 (DPP3) antibody or a dipeptidyl peptidase 3 antibody fragment or DPP3 non-Ig scaffold and means anti-dipeptidyl peptidase 3 (DPP3) antibody or an anti-dipeptidyl peptidase 3 antibody fragment or anti-DPP3 non-Ig scaffold binding to DPP3, respectively.

Throughout the text, the term "antibody" generally comprises monoclonal and polyclonal antibodies and binding fragments thereof, in particular Fc-fragments as well as so called "single-chain-antibodies" (Bird et al. 1988), chimeric, humanized, in particular CDR-grafted antibodies, and di- or tetrabodies (Holliger et al. 1993). Also comprised are immunoglobulin-like proteins that are selected through techniques including, for example, phage display to specifically bind to the molecule of interest contained in a sample.

In this context the term "specific binding" refers to antibodies raised against the molecule of interest or a fragment thereof. An antibody is considered to be specific, if its affinity towards the molecule of interest or the aforementioned fragment thereof is at least preferably 50-fold higher, more preferably 100-fold higher, most preferably at least 1000-fold higher than towards other molecules comprised in a sample containing the molecule of interest. It is well known in the art how to make antibodies and to select antibodies with a given specificity.

"Diseases associated with oxidative stress" with the context of the present invention include, but are not limited to, neurodegenerative diseases, metabolic syndrome, cardiovascular disorders, autoimmune diseases, inflammatory lung diseases, kidney diseases, liver diseases, digestive diseases, viral infectious diseases, cancer, and inflammation, sepsis, septic shock, SIRS.

In the context of the present invention, neurodegenerative diseases comprise Alzheimer's disease (AD), Parkinson's disease (PD), Huntington's disease (HD), amyotrophic lateral sclerosis (ALS) and multiple sclerosis (MS).

In the context of the present invention, metabolic syndrome comprises insulin resistance, obesity, hyperglycemia, dyslipidemia, hypertension and diabetes.

In the context of the present invention, cardiovascular disorders comprise aterosclerosis, hypertension, heart failure, cardiovascular ischemia, cerebral ischemic injury/stroke and myocardial infarction.

In the context of the present invention, autoimmune diseases comprise rheumatoid arthritis and systemic lupus erythematosus.

In the context of the present invention inflammatory lung diseases comprise COPD and asthma.

In the context of the present invention, kidney diseases comprise renal toxicity (drug-induced kidney disease), acute kidney injury (AKI), chronic kidney disease (CKD), diabetic nephropathy and end-stage renal disease (ESRD).

In the context of the present invention, liver diseases comprise hepatotoxicity, viral hepatitis, cirrhosis.

In the context of the present invention, digestive diseases comprise inflammatory bowel disease e.g. Ulcerative colitis, Crohn's disease; gastritis, pancreatitis and peptic ulcer. In this context, viral infectious diseases comprise blood-borne hepatitis viruses (B, C, and D), human immunodeficiency virus (HIV), influenza A, Epstein-Barr virus and respiratory syncytial virus.

In the context of the present invention, cancer comprises prostate cancer, breast cancer, lung cancer, colorectal cancer, bladder cancer, ovarian cancer, skin cancer, stomach cancer and liver cancer.

"Acute condition associated with oxidative stress" with the context of the present invention denote symptoms that appear and change or worsen rapidly due to the occurrence of oxidative stress. An acute condition associated with oxidative stress is sudden in onset. An acute condition associated with oxidative stress may lead to a chronic syndrome, if untreated.

By contrast, a "chronic condition" or a "chronic syndrome", respectively, with the context of the present invention denote a condition or symptom that develops and worsens over an extended period of time, and may be persistent, even if treated.

"Oxidative stress" reflects an imbalance between the systemic manifestation of reactive oxygen species (ROS)/reactive nitrogen species (RNS) and antioxidants in favour of excessive generation of free radicals. This process leads to the oxidation of biomolecules with consequent loss of its biological functions and/or homeostatic imbalances, whose manifestation is the potential oxidative damage to cells and tissues. Accumulation of ROS/RNS can result in a number of deleterious effects such as lipid peroxidation, protein oxidation and DNA damage (including base damage and strand breaks). Further, some reactive oxidative species act as cellular messengers in redox signalling. Thus, oxidative stress can cause disruptions in normal mechanisms of cellular signalling.

A "free radical in the context of" the present invention is a molecule with one or more unpaired electron in its outer shell. Free radicals are formed from molecules via the breakage of a chemical bond such that each fragment keeps one electron, by cleavage of a radical to give another radical and, also via redox reactions. Free radicals related to oxidative stress include hydroxyl (OH.), superoxide ($O_2.^-$), nitric oxide (NO.), nitrogen dioxide ($NO_2.$), peroxyl (ROO.) and lipid peroxyl (LOO.). Also, hydrogen peroxide ($H_2O_2$), ozone ($O_3$), singlet oxygen (1O2), hypochlorous acid (HOCl), nitrous acid ($HNO_2$), peroxynitrite ($ONOO^-$), dinitrogen trioxide ($N_2O_3$), lipid peroxide (LOOH), are not free radicals and generally called oxidants, but can easily lead to free radical reactions in living organisms.

"Primary medicament" means a medicament that acts against the primary cause of said disease or condition.

"Secondary medication" is a medication that improves the condition of the patient in a supportive way; e.g. reduces or regulates oxidative stress which is induced by the administration of a primary medicament.

With the context of the invention, generally the "bioactivity" is defined as the effect that a substance takes on a living organism or tissue or organ or functional unit in vivo or in vitro (e.g. in an assay) after its interaction.

In this regard and specifically with the context of the invention, DPP3 bioactivity may be defined as the DPP3 enzyme activity or the regulating activity of DPP3 in the oxidative stress pathway.

| ABBREVIATIONS | |
|---|---|
| Abbreviation | Meaning |
| aa | amino acid(s) |
| AD | Alzheimer's disease |
| AHF | acute heart failure |
| AIN | Acute interstitial nephritis |
| AKI | acute kidney injury |
| ALD | Alcoholic liver disease |
| ALS | amyotrophic lateral sclerosis |
| ARE | antioxidant response element |
| ATN | Acute tubular necrosis |
| ATP | adenosine triphosphate |
| AZT | Azidothymidin |
| BRCA1 | Breast cancer gene 1 |
| BP | blood pressure |
| BSA | bovine serum albumin |
| cDNA | complementary DNA |
| CAT | catalase |
| CD | Celiac disease |
| CDR | complementarity determining region |
| CKD | chronic kidney disease |
| CLP | cecal ligation and puncture |
| CNS | central nervous system |
| COPD | Chronic obstructive pulmonary disease |
| CSF | Cerebrospinal fluid |
| CVD | cardiovascular diseases |
| DHE | dihydroethidium |
| DN | diabetic nephropathy |
| DNA | Deoxyribonucleic acid |
| DPP3, DPPIII | dipeptidyl dipeptidase 3 |
| DTNB | (5,5'-dithiobis-(2-nitrobenzoic acid), Ellman's reagent |
| EBV | Eppstein Barr virus |
| EC | enzyme category |
| EDTA | Ethylene diamine tetraacetic acid |
| EF | ejection fraction |
| EOC | epithelial ovarian cancer |
| ESRD | end-stage renal disease |
| Fab | Fragment antigen binding |
| Fc | crystallisable fragment |
| FR | framework region |
| GC | Gastric cancer |
| GSH | glutathione |
| GPx | Glutathione peroxidase |
| HBV | Hepatitis B virus |
| HCV | Hepatitis C virus |

ABBREVIATIONS

| Abbreviation | Meaning |
|---|---|
| HD | Huntington's disease |
| hDPP3 | human DPP3 |
| HF | heart failure |
| HFmrEF | heart failure with mid-range ejection fraction |
| HFpEF | heart failure with preserved ejection fraction |
| HFrEF | heart failure with reduced ejection fraction |
| HIV | human immunodeficiency virus |
| HNE | 4-hydroxynonenal |
| IBD | Inflammatory bowel disease |
| i.p | intraperitoneally |
| i.v. | intravenous |
| Ig | immunoglobulin |
| KEAP1 | Kelch like-ECH-associated protein 1 |
| LV | left ventricular |
| LVEF | left ventricular ejection fraction |
| MDA | Malon dialdehyde |
| MS | multiple sclerosis |
| NAFLD | Non-alcoholic fatty liver disease |
| NHS | N-Hydroxysuccinimid |
| non-Ig | non-immunoglobulin |
| NOS | nitric oxide species |
| Nrf2 | nuclear factor erythroid 2-related factor 2 |
| NSAID | Non-steroidal anti-inflammatory drugs |
| o- | ortho |
| OS | Oxidative stress |
| PBS | phosphate buffered saline |
| PD | parkinson's disease |
| PEG | Polyethylene glycole |
| PEG | polyethylene glycole |
| pHMB | polyhexanide, polyhexamethylene biguanide |
| PMSF | phenlymethylsulfonyl fluoride |
| PUD | Peptic ulcer disease |
| RLU | relative light units |
| RNA | Ribonucleic acid |
| RNS | reactive nitrogen species |
| ROI | reactive oxygen intermediates |
| ROS | reactive oxygen species |
| RT | room temperature |
| scFv | single chain variable fragment |
| SDS | sodium dodecyl sulfate |
| SOB | shortness of breath |
| TPCK | tosyl phenylalanin chloromethyl ketone |
| TRX1 | thioreduxin 1 |
| TTE | transthoracic echocardiography |
| UV | ultraviolet |
| XNA | xeno nucleic acid |

EXAMPLES

1. Example 1

Generation of antibodies and determination DPP3 binding ability: Several murine antibodies were produced and screened by their ability of binding human DPP3 in a specific binding assay (see table 3).

1.1. Methods:

—Peptides/Conjugates for Immunization:

DPP3 peptides for immunization were synthesized, see table 3, (JPT Technologies, Berlin, Germany) with an additional N-terminal cystein (if no cystein is present within the selected DPP3-sequence) residue for conjugation of the peptides to Bovine Serum Albumin (BSA). The peptides were covalently linked to BSA by using Sulfolink-coupling gel (Perbio-science, Bonn, Germany). The coupling procedure was performed according to the manual of Perbio. Recombinant GST-hDPP3 was produced by USBio (United States Biological, Salem, Mass., USA).

Immunization of Mice, Immune Cell Fusion and Screening:

Balb/c mice were intraperitoneally (i.p.) injected with 84 µg GST-hDPP3 or 100 µg DPP3-peptide-BSA-conjugates at day 0 (emulsified in TiterMax Gold Adjuvant), 84 µg or 100 µg at day 14 (emulsified in complete Freund's adjuvant) and 42 µg or 50 µg at day 21 and 28 (in incomplete Freund's adjuvant). At day 49 the animal received an intravenous (i.v.) injection of 42 µg GST-hDPP3 or 50 µg DPP3-peptide-BSA-conjugates dissolved in saline. Three days later the mice were sacrificed and the immune cell fusion was performed.

Splenocytes from the immunized mice and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After one week, the HAT medium was replaced with HT Medium for three passages followed by returning to the normal cell culture medium.

The cell culture supernatants were primarily screened for recombinant DPP3 binding IgG antibodies two weeks after fusion. Therefore, recombinant GST-tagged hDPP3 (USBiologicals, Salem, USA) was immobilized in 96-well plates (100 ng/well) and incubated with 50 µl cell culture supernatant per well for 2 hours at room temperature. After washing of the plate, 50 µl/well POD-rabbit anti mouse IgG was added and incubated for 1 h at RT. After a next washing step, 50 µl of a chromogen solution (3.7 mM o-phenylendiamin in citrate/hydrogen phosphate buffer, 0.012% $H_2O_2$) were added to each well, incubated for 15 minutes at RT and the chromogenic reaction stopped by the addition of 50 µl 4N sulfuric acid. Absorption was detected at 490 mm The positive tested microcultures were transferred into 24-well plates for propagation.

After retesting the selected cultures were cloned and recloned using the limiting-dilution technique and the isotypes were determined.

—Mouse Monoclonal Antibody Production

Antibodies raised against GST-tagged human DPP3 or DPP3-peptides were produced via standard antibody production methods (Marx et al. 1997) and purified via Protein A. The antibody purities were ≥90% based on SDS gel electrophoresis analysis.

—Characterization of Antibodies—Binding to hDPP3 and/or Immunization Peptide

To analyze the capability of DPP3/immunization peptide binding by the different antibodies and antibody clones a binding assay was performed:

a) Solid phase

Recombinant GST-tagged hDPP3 (SEQ ID No. 1) or a DPP3 peptide (immunization peptide, SEQ ID No. 2) was immobilized onto a high binding microtiter plate surface (96-Well polystyrene microplates, Greiner Bio-One international AG, Austria, 1 µg/well in coupling buffer [50 mM Tris, 100 mM NaCl, pH7.8], 1 h at RT). After blocking with 5% bovine serum albumin, the microplates were vacuum dried.

b) Labelling Procedure (Tracer)

100 µg (100 µl) of the different antiDPP3 antibodies (detection antibody, 1 mg/ml in PBS, pH 7.4) were mixed with 10 µl acridinium NHS-ester (1 mg/ml in acetonitrile, InVent GmbH, Germany; EP 0 353 971) and incubated for 30 min at room temperature. Labelled antiDPP3 antibody was purified by gel-filtration HPLC on Shodex Protein 5 µm KW-803 (Showa Denko, Japan). The purified labeled antibody was diluted in assay buffer (50 mmol/l potassium phosphate, 100 mmol/l NaCl, 10 mmol/l Nae-EDTA, 5 g/l bovine serum albumin, 1 g/l murine IgG, 1 g/l bovine IgG, 50 µmol/l amastatin, 100 µmol/l leupeptin, pH 7.4). The final concentration was approx. 5-7*10$^6$ relative light units (RLU) of labelled compound (approx. 20 ng labeled antibody) per 200 acridinium ester chemiluminescence was measured by using a Centro LB 960 luminometer (Berthold Technologies GmbH & Co. KG).

c) hDPP3 Binding Assay

The plates were filled with 200 µl of labeled and diluted detection antibody (tracer) and incubated for 2-4 h at 2-8° C. Unbound tracer was removed by washing 4 times with 350 µl washing solution (20 mM PBS, pH 7.4, 0.1% Triton X-100). Well-bound chemiluminescence was measured by using the Centro LB 960 luminometer (Berthold Technologies GmbH & Co. KG).

Characterization of Antibodies—hDPP3-inhibition Analysis

To analyze the capability of DPP3 inhibition by the different antibodies and antibody clones a DPP3 activity assay with known procedure (Jones et al., 1982) was performed. Recombinant GST-tagged hDPP3 was diluted in assay buffer (25 ng/ml GST-DPP3 in 50 mM Tris-HCl, pH7.5 and 100 µM ZnCl$_2$) and 200 µl of this solution incubated with 10 µg of the respective antibody at room temperature. After 1 hour of pre-incubation, fluorogenic substrate Arg-Arg-βNA (20 µl, 2 mM) was added to the solution and the generation of free βNA over time was monitored using the Twinkle LB 970 microplate fluorometer (Berthold Technologies GmbH & Co. KG) at 37° C. Fluorescence of βNA is detected by exciting at 340 nm and measuring emission at 410 nm. Slopes (in RFU/min) of increasing fluorescence of the different samples are calculated. The slope of GST-hDPP3 with buffer control is appointed as 100% activity. The inhibitory ability of a possible capture-binder is defined as the decrease of GST-hDPP3 activity by incubation with said capture-binder in percent.

1.2. Results:

The following table represents a selection of obtained antibodies and their binding rate in Relative Light Units (RLU) as well as their relative inhibitory ability (%; table 3).

The monoclonal antibodies raised against the below depicted DPP3 regions, were selected by their ability to bind recombinant DPP3 and/or immunization peptide, as well as by their inhibitory potential.

All antibodies raised against the GST-tagged, full length form of recombinant hDPP3 show a strong binding to immobilized GST-tagged hDPP3. Also antibodies raised against the SEQ ID 2 peptide bind to GST-hDPP3. The SEQ ID 2 antibodies also strongly bind to the immunization peptide. Those antibodies were characterized in more detail (see example 2). The monoclonal antibody AK1967, with the ability of inhibiting DPP3 activity by 70%, was chosen as possible therapeutic antibody and was also used as template for chimerization and humanization.

TABLE 3 list of antibodies raised against full-length or sequences of hDPP3 and their ability to bind hDPP3 (SEQ ID No. 1) or immunization peptide (SEQ ID No. 2) in RLU, as well as the maximum inhibition of recombinant GST-hDPP3.

| Sequence number | Antigen/ Immunogen | HDPP3 region | Clone | HDPP3 binding [RLU] | immunization peptide binding [RLU] | Max. Inhibition of HDPP3 |
|---|---|---|---|---|---|---|
| SEQ ID: 1 | GST tagged recombinant FL-hDPP3 | 1-737 | 2552 | 3,053,621 | 0 | 65% |
| | | | 2553 | 3,777,985 | 0 | 35% |
| | | | 2554 | 1,733,815 | 0 | 30% |
| | | | 2555 | 3,805,363 | 0 | 25% |
| SEQ ID: 2 | CETVINPETGE QIQSWYRSGE | 474-493 | 1963 | 141,822 | 2,163,038 | 60% |
| | | | 1964 | 100,802 | 2,041,928 | 60% |
| | | | 1965 | 99,493 | 1,986,794 | 70% |
| | | | 1966 | 118,097 | 1,990,702 | 65% |
| | | | 1967 | 113,736 | 1,909,954 | 70% |
| | | | 1968 | 105,696 | 2,017,731 | 65% |
| | | | 1969 | 82,558 | 2,224,025 | 70% |

2. Example 2

Antibodies raised against SEQ ID NO. 2 were characterized in more detail (epitope mapping, binding affinities, specificity, inhibitory potential). Here the results for clone 1967 of SEQ ID NO. 2 ("AK1967") are shown as an example.

2.1. Methods:

—Determination of AK1967 epitope on DPP3:

For epitope mapping of AK1967 a number of N- or C-terminally biotinylated peptides were synthesized (peptides&elephants GmbH, Hennigsdorf, Germany). These peptides include the sequence of the full immunization peptide (SEQ ID No. 2) or fragments thereof, with stepwise removal of one amino acid from either C- or N-terminus (see table 5 for a complete list of peptides).

a) Solid Phase

High binding 96 well plates were coated with 2 µg Avidin per well (Greiner Bio-One international AG, Austria) in coupling buffer (500 mM Tris-HCl, pH 7.8, 100 mM NaCl). Afterwards plate were washed and filled with specific solutions of biotinylated peptides (10 ng/well; buffer—1×PBS with 0.5% BSA)

b) Labelling Procedure (Tracer)

AntiDPP3 antibody AK1967 was labelled with a chemiluminescence label according to Example 1.

c) Peptide Binding Assay

The plates were filled with 200 µl of labeled and diluted detection antibody (tracer) and incubated for 4 h at room temperature. Unbound tracer was removed by washing 4 times with 350 µl washing solution (20 mM PBS, pH 7.4, 0.1% Triton X-100). Well-bound chemiluminescence was measured by using the Centro LB 960 luminometer (Berthold Technologies GmbH & Co. KG). Binding of AK1967 to the respective peptides is determined by evaluation of the relative light units (RLU). Any peptide that shows a significantly higher RLU signal than the unspecific binding of AK1967 is defined as AK1967 binder. The combinatorial analysis of binding and non-binding peptides reveals the specific DPP3 epitope of AK1967.

—Determination of Binding Affinities using Octet:

The experiment was performed using Octet Red96 (ForteBio). AK1967 was captured on kinetic grade anti-humanFc (AHC) biosensors. The loaded biosensors were then dipped into a dilution series of recombinant GST-tagged human DPP3 (100, 33.3, 11.1, 3.7 nM). Association was observed for 120 seconds followed by 180 seconds of dissociation. The buffers used for the experiment are depicted in table 4. Kinetic analysis was performed using a 1:1 binding model and global fitting.

TABLE 4

Buffers used for Octet measurements

| Buffer | Composition |
| --- | --- |
| Assay Buffer | PBS with 0.1% BSA, 0.02% Tween-21 |
| Regeneration Buffer | 10 mM Glycine buffer (pH 1.7) |
| Neutralization Buffer | PBS with 0.1% BSA, 0.02% Tween-21 |

—Western Blot Analysis of Binding Specificity of AK1967:

Blood cells from human EDTA-blood were washed (3× in PBS), diluted in PBS and lysed by repeated freeze-thaw-cycles. The blood cell lysate had a total protein concentration of 250 µg/ml, and a DPP3 concentration of 10 µg/ml. Dilutions of blood cell lysate (1:40, 1:80, 1:160 and 1:320) and of purified recombinant human His-DPP3 (31.25-500 ng/ml) were subjected to SDS-PAGE and Western Blot. The blots were incubated in 1.) blocking buffer (1×PBS-T with 5% skim milk powder), 2.) primary antibody solution (AK1967 1:2.000 in blocking buffer) and 3.) HRP labelled secondary antibody (goat anti mouse IgG, 1:1.000 in blocking buffer). Bound secondary antibody was detected using the Amersham ECL Western Blotting Detection Reagent and the Amersham Imager 600 UV (both from GE Healthcare).

—DPP3 Inhibition Assay:

To analyze the capability of DPP3 inhibition by AK1967 a DPP3 activity assay with known procedure (Jones et al., 1982) was performed. Recombinant GST-tagged hDPP3 was diluted in assay buffer (25 ng/ml GST-DPP3 in 50 mM Tris-HCl, pH7,5) and increasing concentrations of AK1967 were added. Fluorogenic substrate Arg-Arg-βNA was added to the solution and the generation of free βNA over time was monitored using the Twinkle LB 970 microplate fluorometer (Berthold Technologies GmbH & Co. KG) at 37° C. Fluorescence of βNA is detected by exciting at 340 nm and measuring emission at 410 nm. Slopes (in RFU/min) of increasing fluorescence of the different samples are calculated. The slope of GST-hDPP3 with buffer control is appointed as 100% activity. The inhibitory ability AK1967 is defined as the decrease of GST-hDPP3 activity by incubation with said antibody in percent. The resulting lowered DPP3 activities are shown in an inhibition curve in FIG. 1C.

2.2. Results:

—Epitope Mapping:

The analysis of peptides that AK1967 binds to and does not bind to revealed the DPP3 sequence INPETG (SEQ ID No. 3) as necessary epitope for AK1967 binding (see table 5).

TABLE 5

Peptides used for Epitope mapping of AK1967

| peptide ID | peptide sequence | AK1967 binding |
| --- | --- | --- |
| #1 | bio a f n f d q e t v i n p e t g e q i q s w y r s g | yes |
| #2 | bio a f n f d q e t v i n p e t g e q i q | yes |
| #3 | bio a f n f d q e t v i n p e t g e q i | yes |
| #4 | bio a f n f d q e t v i n p e t g e q | yes |
| #5 | bio a f n f d q e t v i n p e t g e | yes |
| #6 | bio a f n f d q e t v i n p e t g | yes |
| #7 | bio a f n f d q e t v i n p e t | no |
| #8 | bio a f n f d q e t v i n p e | no |
| #9 | bio a f n f d q e t v i n p | no |
| #10 | bio a f n f d q e t v i n | no |
| #11 | e t g e q i q s w y k bio | no |
| #12 | p e t g e q i q s w y k bio | no |
| #13 | n p e t g e q i q s w y k bio | no |
| #14 | i n p e t g e q i q s w y k bio | yes |
| #15 | v i n p e t g e q i q s w y k bio | yes |
| #16 | t v i n p e t g e q i q s w y k bio | yes |
| #17 | e t v i n p e t g e q i q s w y k bio | yes |

—Binding Affinity:

AK1967 binds with an affinity of $2.2*10^{-9}$ M to recombinant GST-hDPP3 (for more details see table 6 and for kinetic curves see FIG. 1A).

TABLE 6

Kinetic Constants of AK1967 affinity measurements

| KD (M) | kon(1/Ms) | kdis(1/s) | Full X^2 | Full R^2 |
| --- | --- | --- | --- | --- |
| 2.2E−09 | 1.6E+05 | 3.5E−04 | 0.0413 | 0.9987 |

—Specificity:

The only protein detected with AK1967 as primary antibody in lysate of blood cells was DPP3 at 80 kDa (FIG. 1B). The total protein concentration of the lysate was 250 µg/ml whereas the estimated DPP3 concentration is about 10 µg/ml. Even though there is 25 times more unspecific protein in the lysate, AK1967 binds and detects specifically DPP3 and no other unspecific binding takes place.

—Inhibitory Potential:

AK1967 inhibits 15 ng/ml DPP3 in a specific DPP3 activity assay with an IC50 of about 15 ng/ml (FIG. 1C).

3. Example 3

A septic shock model was used to induce heart failure in rats and then to characterize AK1967's influence on oxidative stress in myocardium.

3.1. Methods:

—Study Design

The study flow is depicted in FIG. 2A below. After CLP or sham surgery the animals were allowed to rest for 20 hours with free access to water and food. Afterwards they were anesthetized, tracheotomy done and arterial and venous line laid. At 24 hours after CLP surgery either AK1967 or vehicle (saline) were administered with 2 mg/kg. As a safety measure hemodynamics were monitored invasively and continuously from t=0 till 3 h.

—CLP Model of Septic Shock

Male Wistar rats (2-3 months, 300 to 400 g, group size refer to table 7) from the Centre d'élevage Janvier (France) were allocated randomly to one of three groups. All the animals were anesthetized using ketamine hydrochloride (90 mg/kg) and xylazine (9 mg/kg) intraperitoneally (i.p.). For induction of polymicrobial sepsis, cecal ligation and puncture (CLP) was performed using Rittirsch's protocol with minor modification. A ventral midline incision (1.5 cm) was made to allow exteriorization of the cecum. The cecum is then ligated just below the ileocecal valve and punctured once with an 18-gauge needle. The abdominal cavity is then closed in two layers, followed by fluid resuscitation (3 ml/100 g body of weight of saline injected subcutaneously) and returning the animal to its cage. Sham animals were subjected to surgery, without getting their cecum punctured.

—Experimentation Time Points and Animal Groups

At t=0 (baseline) all CLP animals are in septic shock and developed a decrease in heart function (low blood pressure, low shortening fraction). At this time point AK1967 (2 mg/kg) or vehicle (saline) were injected (i.v.) and saline infusion was started. There were 1 control group and 2 CLP groups which are summarized in the table below (table 7). At the end of the experiment, the animals were euthanized, and organs (e.g. heart) harvested for subsequent analysis.

TABLE 7 list of experimental groups

| Group | Group size | CLP | treatment |
|---|---|---|---|
| 1 - sham | 4 | no | saline |
| 2 - CLP-saline | 5 | yes | saline |
| 3 - CLP-AK1967 | 5 | yes | AK1967 |

—DHE Labeling of ROS in Myocardium

Dihydroethidium (DHE; Sigma-Aldrich) staining was used to evaluate the in situ levels of superoxide anion in the myocardium. Cardiac cryostat sections (7 μm) of the ventricles were incubated with DHE (37 μM) for 30 min in a dark humidified chamber. Acquisition of fluorescent images of ethidium bromide with Leica fluorescence microscope was performed under identical setting whatever the block tissue. The stained area was measured with IPLab software and expressed as a percentage of area of interest (% of ROI).

3.2. Results:

Rats with septic shock induced heart failure after CLP surgery develop high amounts of reactive oxygen species (ROS) in their myocardium, whereas sham operated animals show almost no oxidative stress (FIGS. 2B and C). Treatment of the sick (CLP) animals with AK1967 reduces the oxidative stress levels in the myocardium to levels of healthy (sham-operated) animals. This strong ROS decrease is achieved within only 3 hours of treatment (FIGS. 2B and C).

REFERENCES

Abramić, M. et al., 2000. Human and rat dipeptidyl peptidase III: Biochemical and mass spectrometric arguments for similarities and differences. Biological Chemistry, 381(December), pp. 1233-1243.

Abramić, M., Zubanović, M. & Vitale, L., 1988. Dipeptidyl peptidase III from human erythrocytes. Biol Chem Hoppe Seyler, pp. 29-38.

Adamczyk B. et al. 2016. New Insights into the Role of Oxidative Stress Mechanisms in the Pathophysiology and Treatment of Multiple Sclerosis. Oxidative Medicine and Cellular Longevity, Vol. 2016, pp. 1-18, DOI: 10.1155/2016/1973834"

Agić, D. et al., 2007. Novel amidino-substituted benzimidazoles: Synthesis of compounds and inhibition of dipeptidyl peptidase III. Bioorganic Chemistry, 35(2), pp. 153-169.

Almagro J C, Fransson J., 2008. Humanization of antibodies. Front Biosci. 2008 Jan. 1; 13:1619-33.

Aoyagi, T. et al., 1993. Enzymatic Changes in Cerebrospinal Fluid of Patients with Alzheimer-Type Dementia. J Clin Biochem Nutr, 14, pp. 133-139.

Balogun, R. A. et al., 2010. Clinical applications of therapeutic apheresis. Journal of clinical apheresis, 25(5), pp. 250-64.

Baršun, M. et al., 2007. Human dipeptidyl peptidase III acts as a post-proline-cleaving enzyme on endomorphins. Biological Chemistry, 388(3), pp. 343-348.

Bhattacharyya A. et al. 2014. Oxidative stress: An essential factor in pathogenesis of gastrointestinal mucosal diseases. Physio.l Rev. 94, pp. 329-354.

Bird et al., 1988. Single-chain antigen-binding proteins. Science 242:423-426.

Chen H. et al. 2011. Oxidative Stress in Ischemic Brain Damage: Mechanisms of Cell Death and Potential Molecular Targets for Neuroprotection. Antioxidants and redox signaling, 14, pp. 1505-1517.

Chen, W. et al., 2009. Direct interaction between Nrf2 and p21Cip1/WAF1 upregulates the Nrf2-mediated antioxidant response. Mol Cell., 34(6), pp. 663-673.

Chiba, T. et al., 2003. Inhibition of recombinant dipeptidyl peptidase III by synthetic hemorphin-like peptides. Peptides, 24(5), pp. 773-778.

Couston, R. G. et al., Adsorption behavior of a human monoclonal antibody at hydrophilic and hydrophobic surfaces. mAbs, 5(1), pp. 126-39.

Deavall, D. G. et al., 2012. Drug-induced oxidative stress and toxicity. J Toxicol, pp. 645460.

Deng, B. et al., 2014. Aptamer binding assays for proteins: The thrombin example—A review. Analytica Chimica Acta, 837, pp. 1-15.

Dhanda, S., Singh, J. & Singh, H., 2008. Hydrolysis of various bioactive peptides by goat brain dipeptidylpeptidase-III homologue. Cell biochemistry and function, 26(3), pp. 339-45.

Elahi M. M. et al. 2009. Oxidative stress as a mediator of cardiovascular disease. Oxidative Medicine and Cellular Longevity, 2:5, pp. 259-269.

Ellis, S. & Nuenke, J. M., 1967. Dipeptidyl Arylamidase III of the Pituitary: Purification and Characterization. Journal of Biological Chemistry, 242(20), pp. 4623-4629.

Gamrekelashvili, J. et al., 2013. Peptidases released by necrotic cells control CD8+ T cell cross-priming. journal of clinical investigation, 123(11), pp. 4755-4768.

Hartley et al, 1982. Radiology 143: 29-36

Hast B. E. et al., 2013. Proteomic analysis of ubiquitin ligase KEAP1 reveals associated proteins that inhibit NRF2 ubiquitination. Cancer Res., 73(7), pp. 2199-2210.

Hast B. E. et al., 2014. Cancer-Derived Mutations in KEAP1 Impair NRF2 Degradation but not Ubiquitination. Molecular and Cellular Pathobiology. Cancer research, 74 (3), pp. 808-817.

Holguin F. 2013. Oxidative Stress in Airway Diseases. Ann. Am. Thorac. Soc., Vol 10, Supplement, pp. S150-S157.

Holliger P. et al. (1993) Proc. Natl. Acad. Sci. U.S.A. 90:6444-8

Hood et al., Immunology, Benjamin, N.Y., 2nd ed., 1984

Hori M. et al. 2009, Oxidative stress and left ventricular remodelling after myocardial infarction. Cardiovascular research, 81, pp. 457-464.

Hosohata K. 2016. Role of Oxidative Stress in Drug-Induced Kidney Injury. International Journal of Molecular Sciences, 17, pp. 1826-1836.

Hultschig C et al., Curr Opin Chem Biol. 2006 February; 10(1):4-10. PMID: 16376134)

Hunkapiller & Hood, 1986. The growing immunoglobulin gene superfamily. Nature 323:15-16.

Hust, M., Meyer, T., Voedisch, B., Rülker, T., Thie, H., El-Ghezal, A., Kirsch, M. I., Schütte, M., Helmsing, S., Meier, D., Schirrmann, T., Dübel, S., 2011. A human scFv antibody generation pipeline for proteome research. Journal of Biotechnology 152,159-170

Huston et al., 1988. Protein engineering of antibody binding sites: recovery of specific activity in an anti-digoxin single-chain Fv analogue produced in *Escherichia coli*. Proc. Natl. Acad. Sci. U.S.A., 85:5879-5883.

Hutcheson R. et al. The Metabolic Syndrome, Oxidative Stress, Environment, and Cardiovascular Disease: The Great Exploration. Experimental Diabetes Research, Vol. 2012, Article ID 271028.

Igic, R. & Behnia, R., 2007. Pharmacological, immunological, and gene targeting of the renin-angiotensin system for treatment of cardiovascular disease. Current pharmaceutical design, 13(12), pp. 1199-214.

Inaoka, Y. & Naruto, S., 1988. Propioxatins A and B, New Enkephalinase B Inhibitors, IV. Characterization of the Active Site of the Enzyme Using Synthetic Propioxatin Analogues. J. Biochem, 104(5), pp. 706-711.

Ivanov A. V. et al. 2017. Oxidative Stress in Infection and Consequent Disease. Oxidative Medicine and Cellular Longevity, Vol. 2017, Article ID 3496043.

Ivanov A. V. et al. 2017. Oxidative stress, a trigger of hepatitis C and B virus-induced liver carcinogenesis. Oncotarget, 8, pp. 3895-3932.

Jones, T. H. & Kapralou, A, 1982. A rapid assay for dipeptidyl aminopeptidase III in human erythrocytes. Analytical biochemistry, 119(2), pp. 418-23.

Kabat et al., 1983. Sequences of Proteins of Immunological Interest, U.S. Department of Health and Human Services.

Kaymak C. et al. 2011. Reactive Oxygen Species (Ros) Generation in Sepsis. FABAD J. Pharm. Sci., 36, pp. 41-47.

Khaket, T. P. et al., 2012. Enkephalin degrading enzymes: metalloproteases with high potential for drug development. Current pharmaceutical design, 18(2), pp. 220-30.

Khandrika L. et al. 2009. Role of Oxidative Stress in Prostate Cancer. Cancer Lett., 282(2), pp. 125-136.

Kim, D. & Herr, A. E., 2013. Protein immobilization techniques for microfluidic assays. Biomicrofluidics, 7(4), p. 41501.Kirk-Othmer, Encyclopedia of chemical technology, 4th ed., executive editor, J. I. Kroschwitz; editor, M. Howe-Grant, John Wiley & Sons, 1993, vol. 15, p. 518-562

Kruk J. et al. 2017. Reactive Oxygen and Nitrogen Species in Carcinogenesis: Implications of Oxidative Stress on the Progression and Development of Several Cancer Types. Mini-Reviews in Medicinal Chemistry, 17, pp. 904-919.

Kumar, P. et al., 2016. Substrate complexes of human dipeptidyl peptidase III reveal the mechanism of enzyme inhibition. Scientific Reports, 6(March), p. 23787.

Lanzavecchia, A. & Scheidegger, D., 1987. The use of hybrid hybridomas to target human cytotoxic T lymphocytes, Eur. J. Immunol. 17:105.

Lee, C. M. & Snyder, S. H., 1982. Dipeptidyl-aminopeptidase III of rat brain. Selective affinity for enkephalin and angiotensin. The Journal of biological chemistry, 257(20), pp. 12043-50.

Li S. et al. 2015. The Role of Oxidative Stress and Antioxidants in Liver Diseases. International Journal of Molecular Sciences, 16, pp. 26087-26124.

Li, J. et al., 2011. Peptide aptamers with biological and therapeutic applications. Current medicinal chemistry, 18(27), pp. 4215-22.

Liu Z. et al. 2017. Oxidative Stress in Neurodegenerative Diseases: From Molecular Mechanisms to Clinical Applications. Oxidative Medicine and Cellular Longevity, Vol. 2017, Article ID 2525967.

Liu, Y. et al., 2007. A genomic screen for activators of the antioxidant response element. Proceedings of the National Academy of Sciences of the United States of America, 104(12), pp. 5205-10.

Lu K. et al., 2017. NRF2 induction supporting breast cancer cell survival is enabled by oxidative stress-induced DPP3-KEAP2 interaction. OnlineFirst; DOI: 10.1158/0008-5472.CAN-16-2204.

Ma Q. et al., Role of Nrf2 in Oxidative Stress and Toxicity. Annu Rev Pharmacol Toxicol., 53, pp. 401-426.

Ma Y. et al. 2013, Relation between Gastric Cancer and Protein Oxidation, DNA Damage, and Lipid Peroxidation. Oxidative Medicine and Cellular Longevity, Vol. 2013, Article ID 543760.

Marx et al., 1997. Monoclonal Antibody Production, ATLA 25, 121.

Mazzocco, C. et al., 2006. Identification and characterization of two dipeptidyl-peptidase III isoforms in Drosophila melanogaster. FEBS Journal, 273(5), pp. 1056-1064.

Meliopoulos, V. A. et al., 2012. MicroRNA regulation of human protease genes essential for influenza virus replication. PloS one, 7(5), p.e37169.

Müller, J. et al., 2012. Monitoring of plasma levels of activated protein C using a clinically applicable oligonucleotide-based enzyme capture assay. Journal of Thrombosis and Haemostasis, 10(3), pp. 390-398.

Müller, J. et al., 2016. Aptamer-Based Enzyme Capture Assay for Measurement of Plasma Thrombin Levels. Methods in molecular biology (Clifton, N.J.), 1380, pp. 179-89.

Narendhirakannan R. T. et al., 2012. Oxidative Stress and Skin Cancer: An Overview. Ind. J. Clin. Biochem., 28, pp. 110-115.

Nourazarian A. R. et al., 2014. Roles of Oxidative Stress in the Development and Progression of Breast Cancer. Asian Pac. J. Cancer Prev., 15 (12), pp. 4745-4751

Ohkubo, I. et al., 1999. Dipeptidyl peptidase III from rat liver cytosol: purification, molecular cloning and immunohistochemical localization. Biological chemistry, 380(12), pp. 1421-1430.

Patel, A., Smith, H. J. & Sewell, R. D., 1993. Inhibitors of enkephalin-degrading enzymes as potential therapeutic agents. Progress in medicinal chemistry, 30, pp. 327-78.

Perl A. 2013. Oxidative stress in the pathology and treatment of systemic lupus erythematosus. Nat. Rev. Rheumatol., 9(11), pp. 674-686.

Perse M., 2013. Oxidative Stress in the Pathogenesis of Colorectal Cancer: Cause or Consequence?. BioMed Research International, Vol. 2013, Article ID 725710.

Pham-Huy et al. 2008. Free Radicals, Antioxidants in Disease and Health. Int. J. Biomed. Sci., 4 (2), pp. 89-96.

Pinheiro Da Silva, F. & Nizet, V., 2009. Cell death during sepsis: Integration of disintegration in the inflammatory response to overwhelming infection. Apoptosis, 14(4), pp. 509-521.

Pitocco et al. 2013. Oxidative Stress in Diabetes: Implications for Vascular and Other Complications. Int. J. Mol. Sci., 14, pp. 21525-21550.

Pohanka M. 2013. Role of oxidative stress in infectious diseases. A review. Folia Microbiol., 58, pp. 503-513.

Prajapati, S. C. & Chauhan, S. S., 2011. Dipeptidyl peptidase III: a multifaceted oligopeptide N-end cutter. FEBS Journal, 278(18), pp. 3256-3276.

Quiñonez-Flores C. M. 2016, Oxidative Stress Relevance in the Pathogenesis of the Rheumatoid Arthritis: A Systematic Review. BioMed Research International Volume 2016, Article ID 6097417.

Raghupathi, R., 2004. Cell death mechanisms following traumatic brain injury. Brain pathology (Zurich, Switzerland), 14(2), pp. 215-22.

Rastija, V. et al., 2015. Synthesis, QSAR, and Molecular Dynamics Simulation of Amidino-substituted Benzimidazoles as Dipeptidyl Peptidase III Inhibitors. Acta Chimica Slovenica, 62, pp. 867-878.

Rittirsch, D., Huber-Lang, M., Flierl, M. Ward, P.: Immunodesign of experimental sepsis by cecal ligation and punc-ture, Nature Protocols 4,-31-36 (2009)

Rodrigo R. et al., 2013. Oxidative Stress and Pathophysiology of Ischemic Stroke: Novel Therapeutic Opportunities. CNS & Neurological Disorders—Drug Targets, DOI: 10.2174/1871527311312050015.

Romanillos, G. et al. EP 2949332 A2

Saed G. M. et al., 2017. Updates of the role of oxidative stress in the pathogenesis of ovarian cancer. Gynecologic Oncology, 145, pp. 595-602.

Sanderink, G. J., Artur, Y. & Siest, G., 1988. Human aminopeptidases: a review of the literature. Journal of clinical chemistry and clinical biochemistry. Zeitschrift für klinische Chemie and klinische Biochemie, 26(12), pp. 795-807.

Sawicka E. et al. 2015. The role of oxidative stress in bladder cancer, Postepy Hig Med Dosw, 69, pp. 744-752.

Schütte, M., Thullier, P., Pelat, T., Wezler, X., Rosenstock, P., Hinz, D., Kirsch, M. I., Hasenberg, M., Frank, R., Schirrmann, T., Gunzer, M., Hust, M., Dübel, S., 2009. Identification of a putative Crf splice variant and generation of recombinant antibodies for the specific detection of Aspergillus fumigatus. PLoS One 4, e6625

Schwarz K. B. 1996, Oxidative stress during viral infection. Free Radical Biology & Medicine, 21, No. 5, pp. 641-649.

Shimamori, Y., Watanabe, Y. & Fujimoto, Y., 1986. Purification and Characterization of Dipeptidyl Aminopeptidase III from Human Placenta. Chem. Pharm. Bull., 34(8), pp. 3333-3340.

Šimaga, Š. et al., 1998. Dipeptidyl peptidase III in malignant and non-malignant gynaecological tissue. European Journal of Cancer, 34(3), pp. 399-405.

Šimaga, Š. et al., 2003. Tumor cytosol dipeptidyl peptidase III activity is increased with histological aggressiveness of ovarian primary carcinomas. Gynecologic Oncology, 91(1), pp. 194-200.

Singh, R. et al., 2014. Transcription factor C/EBP-beta mediates downregulation of dipeptidyl-peptidase III expression by interleukin-6 in human glioblastoma cells. FEBS Journal, 281, pp. 1629-1641.

Sobocanec et al., 2015. The role of 17β-estradiol in the regulation of antioxidant enzymes via the Nrf2-Keap1 pathway in the livers of CBA/H mice. Life Sciences, 130, pp. 57-65

Sobocanec et al., 2016. Prominent role of exopeptidase DPP III in estrogen-mediated protection against hyperoxia in vivo. Redox Biology, 8, pp. 49-159

Sosa et al. 2013. Oxidative stress and cancer: An overview. Ageing Research Reviews, 12, pp. 376-390.

Sureshbabu A. 2015. Oxidative stress and autophagy: Crucial modulators of kidney injury. Redox Biology, 4, pp. 208-214.

Tian T. et al. 2017. Pathomechanisms of Oxidative Stress in Inflammatory Bowel Disease and Potential Antioxidant Therapies. Oxidative Medicine and Cellular Longevity, Vol. 2017, Article ID 4535194.

Ullah A. et al. 2015. Diabetes mellitus and oxidative stress—A concise review. Saudi Pharmaceutical Journal, 24, pp. 547-553.

Vairappan B. 2015. Endothelial dysfunction in cirrhosis: Role of inflammation and oxidative stress. World Journal of Hepatology, 7 (3), pp. 443-459.

Valavanidis A. et al. 2013, Pulmonary Oxidative Stress, Inflammation and Cancer: Respirable Particulate Matter, Fibrous Dusts and Ozone as Major Causes of Lung Carcinogenesis through Reactive Oxygen Species Mechanisms. Int. J. Environ. Res. Public Health, 10, pp. 3886-3907.

Vandenberg, I., King, F. & Kuchel, P., 1985. Enkephalin Degradation by Human Erythrocytes and Hemolysates Studied Using 1H NMR Spectroscopy. Archives of Biochemistry and Biophysics, 242(2), pp. 515-522.

Vanha-Perttula, T., 1988. Dipeptidyl peptidase III and alanyl aminopeptidase in the human seminal plasma: origin and biochemical properties. Clinica chimica acta; international journal of clinical chemistry, 177(2), pp. 179-95.

Volonte, D. et al., 2013. Inhibition of nuclear factor-erythoid 2-related factor (Nrf2) by caveolin-2 promotes stress-induced premature senescence. Molecular Biology of the Cell, 24, pp. 1852-1862.

Wang Z. et al., 2016. Oxidative Stress and Liver Cancer: Etiology and Therapeutic Targets. Oxidative Medicine and Cellular Longevity, Vol. 2016, Article ID: 7891574.

Wattiaux, R. et al., 2007. Lysosomes and Fas-mediated liver cell death. The Biochemical journal, 403(1), pp. 89-95.

Wild, David (2005). The Immunoassay Handbook, Elsevier LTD, Oxford; 3rd ed., ISBN-13: 978-0080445267

Xu, Y., Yang, X. & Wang, E., 2010. Review: Aptamers in microfluidic chips. Analytica chimica acta, 683(1), pp. 12-20.

Yamamoto, Y. et al., 1998. Inhibitory action of spinorphin, an endogenous regulator of enkephalin-degrading enzymes, on carrageenan-induced polymorphonuclear neutrophil accumulation in mouse air-pouches. Life sciences, 62(19), pp. 1767-73.

Yamamoto, Y. et al., 2000. Characterization of tynorphin, a potent endogenous inhibitor of dipeptidyl peptidaseIII. Peptides, 21(4), pp. 503-8.

Zong, W.-X. & Thompson, C. B., 2006. Necrotic Cell Death as a Cell Fate. Genes & Development, 20, pp. 1-5.

Zuk et al., Enzyme Immunochromatography—A Quantitative Immunoassay Requiring No Instrumentation, Clinical Chemistry, 31 (7): 1144-1150 (1985)

SEQUENCE LISTING

SEQ ID No. 1-hDPP3 aa 1-737
MADTQYILPNDIGVSSLDCREAFRLLSPTERLYAYHLSRAAWYGGLAVLLQTSPEAP
YIYALLSRLFRAQDPDQLRQHALAEGLTEEEYQAFLVYAAGVYSNMGNYKSFGDTK
FVPNLPKEKLERVILGSEAAQQHPEEVRGLWQTCGELMFSLEPRLRHLGLGKEGITTY
FSGNCTMEDAKLAQDFLDSQNLSAYNTRLFKEVDGEGKPYYEVRLASVLGSEPSLDS
EVTSKLKSYEFRGSPFQVTRGDYAPILQKVVEQLEKAKAYAANSHQGQMLAQYIESF
TQGSIEAHKRGSRFWIQDKGPIVESYIGFIESYRDPFGSRGEFEGFVAVVNKAMSAKFE
RLVASAEQLLKELPWPPTFEKDKFLTPDFTSLDVLTFAGSGIPAGINIPNYDDLRQTEG
FKNVSLGNVLAVAYATQREKLTFLEEDDKDLYILWKGPSFDVQVGLHELLGHGSGK
LFVQDEKGAFNFDQETVINPETGEQIQSWYRSGETWDSKFSTIASSYEECRAESVGLY
LCLHPQVLEIFGFEGADAEDVIYVNWLNMVRAGLLALEFYTPEAFNWRQAHMQARF
VILRVLLEAGEGLVTITPTTGSDGRPDARVRLDRSKIRSVGKPALERFLRRLQVLKSTG
DVAGGRALYEGYATVTDAPPECFLTLRDTVLLRKESRKLIVQPNTRLEGSDVQLLEY
EASAAGLIRSFSERFPEDGPELEEILTQLATADARFWKGPSEAPSGQA

SEQ ID No. 2-hDPP3 aa 474-493 (N-Cys)-immunization peptide with
additional N-terminal Cystein
CETVINPETGEQIQSWYRSGE SEQ ID No. 3-hDPP3 aa 477-482-epitope of AK1967
INPETG SEQ ID No. 4-hDPP3 aa 480-483
ETGE SEQ ID No. 5-variable region of murine AK1967 in heavy chain
QVTLKESGPGILQPSQTLSLTCSFSGFSLSTSGMSVGWIRQPSGKGLEWLAHIWWNDN
KSYNPALKSRLTISRDTSNNQVFLKIASVVTADTGTYFCARNYSYDYWGQGTTLTVSS SEQ ID No. 6-variable region of murine AK1967 in light chain
DVVVTQTPLSLSVSLGDPASISCRSSRSLVHSIGSTYLHWYLQKPGQSPKLLIYKVSNR
FSGVPDRFSGSGSGTDFTLKISRVEAEDLGVYFCSQSTHVPWTFGGGTKLEIK SEQ ID No. 7-CDR1 of murine AK1967 in heavy chain
GFSLSTSGMS SEQ ID No. 8-CDR2 of murine AK1967 in heavy chain
IWWNDNK SEQ ID No. 9-CDR 3 of murine AK1967 in heavy chain
ARNYSYDY SEQ ID No. 10-CDR1 of murine AK1967 in light chain
RSLVHSIGSTY CDR2 of murine AK1967 in light chain
KVS SEQ ID No. 11-CDR3 of murine AK1967 in light chain
SQSTHVPWT SEQ ID No. 12-humanized AK1967-heavy chain sequence (IgG1κ backbone)
MDPKGSLSWRILLFLSLAFELSYGQITLKESGPTLVKPTQTLTLTCTFSGFSLSTSGMS
VGWIRQPPGKALEWLAHIWWNDNKSYNPALKSRLTITRDTSKNQVVLTMTNMDPV
DTGTYYCARNYSYDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALH
NHYTQKSLSLSPG SEQ ID No. 13-humanized AK1967-light chain sequence (IgG1κ backbone)
METDTLLLWVLLLWVPGSTGDIVMTQTPLSLSVTPGQPASISCKSSRSLVHSIGSTYLY
WYLQKPGQSPQLLIYKVSNRFSGVPDRFSGSGSGTDFTLKISRVEAEDVGVYYCSQST
HVPWTFGGGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVT
KSFNRGEC

FIGURE DESCRIPTION

FIG. 1: AK1967 characterization (A) Association- and dissociation curve of the AK1967-DPP3 binding analysis using Octet. AK1967 loaded biosensors were dipped into a dilution series of recombinant GST-tagged human DPP3 (100, 33.3, 11.1, 3.7 nM) and association and dissociation monitored.

(B) Western Blot of dilutions of blood cell lysate and detection of DPP3 with AK1967 as primary antibody.

(C) Inhibition curve of native DPP3 from blood cells with inhibitory antibody AK1967. Inhibition of DPP3 by a specific antibody is concentration dependent, with an $IC_{50}$ at ~15 ng/ml when analyzed against 15 ng/ml DPP3.

Figure 2:
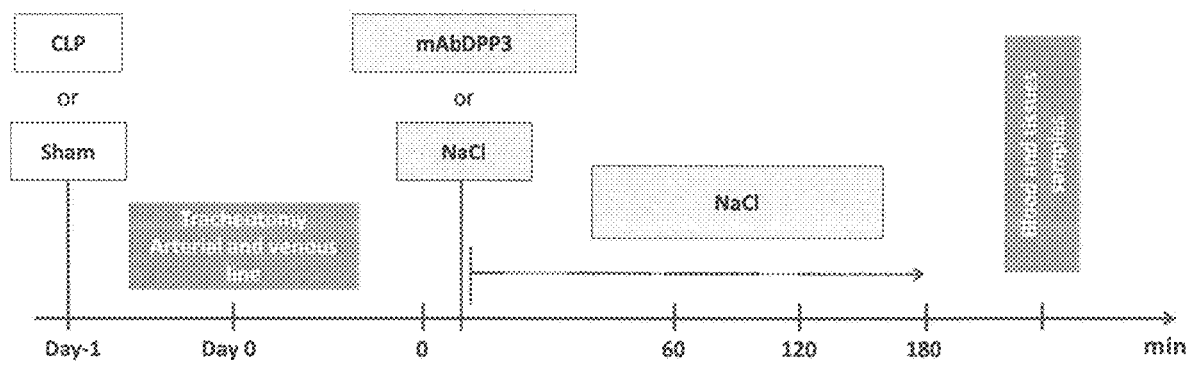
Figure 2:
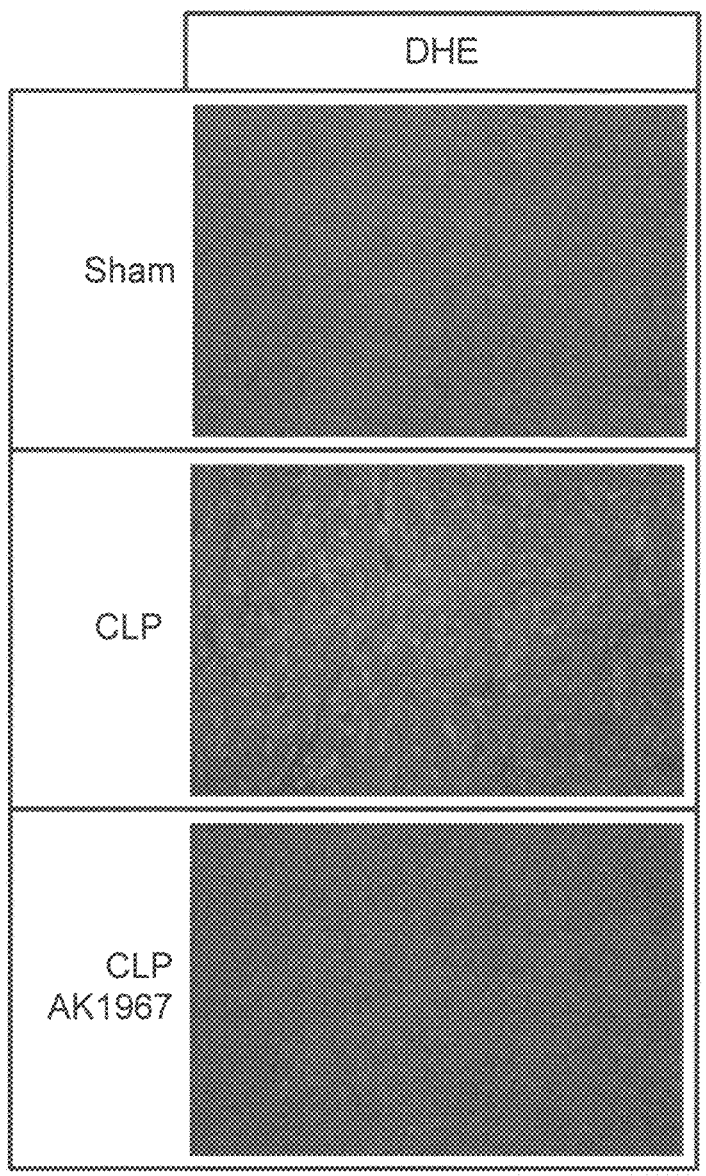
Figure 2:
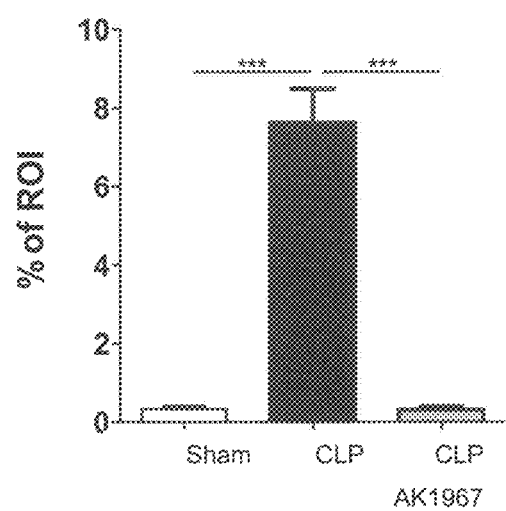

FIG. 2: Influence of AK1967 on oxidative stress in rats with septic shock induced heart failure (A) Experimental design of heart failure study of rats in septic shock.
(B) Fluorescence images of DHE labelled myocardium of sham, CLP and CLP AK1967 animals.
(C) Quantification of DHE stained areas and expression as percentage of area of interest (% of ROI).

The invention claimed is:

1. A dipeptidyl peptidase 3 (DPP3) binder directed to and binding to an epitope according to SEQ ID NO.: 2, and wherein said DPP3 binder recognizes and binds to at least three amino acids of SEQ ID NO.: 2, wherein said epitope is comprised in SEQ ID NO.: 1, and wherein said DPP3 binder exhibit an affinity towards DPP3 in such that the affinity constant is at least $10^7$ M$^{-1}$, wherein said DPP3 binder is a monoclonal antibody or antigen binding fragment, and wherein the complementarity determining regions (CDR's) in the heavy chain comprises the sequences:

SEQ ID NO.: 7, SEQ ID NO.:8 and SEQ ID NO.: 9

And the complementarity determining regions (CDR's) in the light chain comprises the sequences:

SEQ ID.: 10, KVS and SEQ ID NO.: 11.

2. The dipeptidyl peptidase 3 binder directed to and binding to an epitope according to SEQ ID NO.: 2 of claim 1, wherein said DPP3 binder is directed to and binding to an epitope according to SEQ ID NO.: 3, and wherein said DPP3 binder recognizes and binds to at least three amino acids of SEQ ID NO.: 3.

3. The dipeptidyl peptidase 3 binder directed to and binding to an epitope according to SEQ ID NO.: 2 of claim 1, wherein said DPP3 binder is directed to and binding to an epitope according to SEQ ID NO.: 4, and wherein said DPP3 binder recognizes and binds to at least three amino acids, of SEQ ID NO.: 4.

4. The dipeptidyl peptidase 3 binder directed to and binding to an epitope according to SEQ ID NO.: 2 of claim 1, wherein said DPP3 binder is selected from a group comprising an antibody or antigen binding fragment or non-Ig scaffold.

5. The dipeptidyl peptidase 3 binder directed to and binding to an epitope according to SEQ ID NO.: 2 of claim 1, wherein said DPP3 binder is selected from a group comprising a monospecific antibody or a antigen binding fragment or a monospecific non-Ig scaffold.

6. The dipeptidyl peptidase 3 binder directed to and binding to an epitope according to SEQ ID NO.: 2 of claim 1, wherein said DPP3 binder is a humanized monoclonal antibody or antigen binding fragment, wherein the heavy chain comprises the sequence: SEQ ID NO.: 12 and wherein the light chain comprises the sequence: SEQ ID NO.: 13.

\* \* \* \* \*